United States Patent
Gupta et al.

(10) Patent No.: US 12,377,082 B2
(45) Date of Patent: *Aug. 5, 2025

(54) NICORANDIL DERIVATIVES

(71) Applicant: UNICYCIVE THERAPEUTICS INC., Los Altos, CA (US)

(72) Inventors: Shalabh Gupta, Mountain View, CA (US); Sundeep Dugar, San Jose, CA (US)

(73) Assignee: UNICYCIVE THERAPEUTICS INC., Los Altos, CA (US)

( * ) Notice: Subject to any disclaimer, the term of this patent is extended or adjusted under 35 U.S.C. 154(b) by 921 days.

This patent is subject to a terminal disclaimer.

(21) Appl. No.: 17/439,781

(22) PCT Filed: Mar. 16, 2020

(86) PCT No.: PCT/US2020/023016
§ 371 (c)(1),
(2) Date: Sep. 15, 2021

(87) PCT Pub. No.: WO2020/190890
PCT Pub. Date: Sep. 24, 2020

(65) Prior Publication Data
US 2022/0265630 A1  Aug. 25, 2022

Related U.S. Application Data

(60) Provisional application No. 62/819,372, filed on Mar. 15, 2019.

(51) Int. Cl.
*A61K 31/4425* (2006.01)
*A61K 31/4545* (2006.01)
*A61K 31/455* (2006.01)
*A61P 13/12* (2006.01)

(52) U.S. Cl.
CPC ...... *A61K 31/4425* (2013.01); *A61K 31/4545* (2013.01); *A61K 31/455* (2013.01); *A61P 13/12* (2018.01)

(58) Field of Classification Search
CPC .............. A61K 31/455; A61K 31/4425; A61K 31/4545; A61P 13/12; C12Q 1/6886; C12Q 2600/118; C12Q 2600/154
See application file for complete search history.

(56) References Cited

U.S. PATENT DOCUMENTS

2011/0257202 A1* 10/2011 Johnson ............... A61P 3/04
514/355

FOREIGN PATENT DOCUMENTS

JP    H11-106352 A    4/1999
WO   WO 2012/137225 A1  10/2012

OTHER PUBLICATIONS

International Search Report and Written Opinion mailed Jul. 15, 2021 for Application No. PCT/US2020/023016; 15 pages.
Fan, et al: "Preventive effect of oral nicorandil on contrast-induced nephropathy in patients with renal insufficiency undergoing elective cardiac catheterization", Heart Vessels; Feb. 13, 2016; vol. 31, pp. 1776-1782.
Nawa, et al: "Continuous intravenous infusion of nicorandil for 4 hours before and 24 hours after percutaneous coronary intervention protects against contrast-induced nephropathy in patients with poor renal function", International Journal of Cardiology; May 22, 2015; vol. 195, pp. 228-234.
Notice of Reasons for Rejection mailed Feb. 16, 2024, for Japanese Patent Application No. 2021-578168, with Engligh translations, 9 pages.
Iranirad et al., "Efficacy of nicorandil treatment for prevention of contrast-induced nephropathy in high-risk patients undergoing cardiac catheterization: A prospective randomized controlled trial", Cardiol J., 2017, vol. 24(5), pp. 502-507.
Written Opinion mailed Mar. 28, 2023, for Singapore Patent Application No. 11202109899V, 8 pages.
Tamura et al., "Nicorandil, a $K_{atp}$ channel opener, alleviates chronic renal injury by targeting podocytes and macrophages", Am J Physiol Renal Physiol, 2012, vol. 303, F339-349.
Tanabe et al., "Nicorandil as a novel therapy for advanced diabetic nephropathy in the eNOS-deficient mouse", Am J Physiol Renal Physiol, 2012, vol. 302(9), pp. F1151-F1160.

* cited by examiner

*Primary Examiner* — Umamaheswari Ramachandran
(74) *Attorney, Agent, or Firm* — Squire Patton Boggs (US) LLP

(57) ABSTRACT

Disclosed herein are pyridyl compounds. Also described are specific conjugated nicorandil compounds. Also disclosed are pharmaceutical compositions that include the compounds. Methods of using the pyridyl compounds are disclosed for the treatment of diseases or conditions related to kidney or kidney functions.

14 Claims, 2 Drawing Sheets
Specification includes a Sequence Listing.

NICORANDIL DERIVATIVES

CROSS-REFERENCE TO RELATED APPLICATION

This application is a U.S. national phase entry of International Patent Application No. PCT/US2020/023016, filed Mar. 16, 2020, which claims priority to U.S. Application No. 62/819,372 filed on Mar. 15, 2019. The contents of both related applications are incorporated herein by reference in their entirety.

INCORPORATION-BY-REFERENCE

This application includes an electronically submitted sequence listing in .txt format. The .txt file contains a sequence listing entitled "118662_00020_SequenceListing.txt" which was created on May 6, 2022 and is 1,420 bytes in size. The sequence listing contained in this .txt file is part of the specification and is herein incorporated by reference in its entirety.

FIELD OF THE INVENTION

Described herein are compounds, pharmaceutical compositions and medicaments containing such compounds, and methods of using such compounds and compositions for treating diseases or conditions related to kidney or kidney functions.

BACKGROUND OF THE INVENTION

Kidney diseases such as Chronic Kidney Disease, Acute kidney failure and Acute Kidney disease are major health concerns in USA. Approximately 20 million people in the United States are currently affected by chronic kidney disease (CKD), with half a million of these diagnosed with the most severe form of known as end-stage renal disease (ESRD). One of the major causes of chronic and ESRD in the United States is diabetes, which results in approximately 50% of all cases. Apart from Diabetes, hypertension and cardiovascular disease remains the leading cause of death for patients with CKD. Similar to CKD, Acute Kidney Injury (AKI), Acute Kidney Failure (AKF) & diabetic nephropathy which eventually progresses into CKD are also debilitating kidney diseases that affect millions of people in USA as well as outside USA. AKI is a relatively common condition in the intensive care unit and occurs in 20% to 30% of critically ill patients, with approximately 6% eventually requiring renal replacement therapy (1). The development of AKI results in increased mortality, longer length of stay in hospitals and eventually, increased healthcare costs (2). While in most of the cases the epidemiological causes of AKI is multifactorial (e.g., sepsis, ischemia/hypoperfusion), recent studies have shown that nephrotoxic drugs will be contributing factors in 19% to 25% of cases of severe acute renal failure in patients with serious underlying diseases (3, 4). The use of nephrotoxic drugs and resulting Acute Kidney Injury is referred to as Drug Induced AKI which is a major problem with patients taking drugs such as antibiotics, anticancer agents and anti-infectious drugs Treatment options for CKD, AKI or AKF range from Renal Replacement Therapy (RRT), Transplant & radical surgery. Angiotensin Converting Enzyme Inhibitors (ACEI) or Angiotensin Receptor Blockers (ARBs) or protein-restricted diet have been used in certain conditions to mitigate the effect of these kidney diseases. However, in majority of the cases the damage is irreversible and the patient needs to have transplant or be on dialysis for remainder of their life. The following is summary of drugs that are currently being used or developed for CKD. Renin Inhibitors—Aliskerin, ACE inhibitors—Captopril, Ramipril and Lisinopril, Angiotensin receptor inhibitors-Telmisartan, Losartan, Mineralcorticoid antagonists-Spironolactone, Finerenone, CS-3150 and MT-3995. Drugs that target Glomerulus abnormalities such as sulodexide, Atrasentan, Abatacept, Bis-T-23, rapamycin, lithium and gamma-secretase inhibitors. A large number of drugs are currently under clinical development for variety of pathways and targets that result in CKD. These drugs are Canagliflozin, Pyridorin, ASP8232, baricitinib, CCX140, CTP140, GKT137831, VPI-2690B, GS-4997, PF-04634817, and Allopurinol.

Nicorandil is a vasodilatory drug used to treat angina and acute heart failure. It is a nitrate and K+ATP channel agonist. In addition to treat angina, nicorandil may be useful to treat kidney diseases (Lee et al., J. Hypertension 2009, 27, 618-625; Iranirad et al., Cardiology Journal (online) 2017, DOI 10.5603/cj.a2017.0028; Ko et al., Yonsei Med J. 2013, 54(4), 957-964; Tamura et al., Am. J. Physiol Renal Physiol 2012, 303, 339-349; Nawa et al., Int. J. Cardiology 2015, 195, 228-234; Tanabe et al., Am. J. Physiol Renal Physiol 2012, 302, 151-160; and US20110257202).

SUMMARY OF THE INVENTION

Described herein are pyridyl compounds and pharmaceutical compositions thereof. Also described herein are methods for treating diseases and conditions related to kidney using the compounds and pharmaceutical compositions.

Also described herein are uses of the pyridyl compounds and the pharmaceutical compositions in the treatment of kidney diseases or conditions. Further described are pharmaceutical compositions that include the pyridyl compounds. Specifically, described herein are conjugated nicorandil compounds capable of forming nicorandil in vivo and methods of use thereof to treat diseases and conditions related to kidney.

Thus, in some embodiments, the present invention provides methods for preventing, treating or ameliorating in a mammal a disease or condition that is related to the kidney or kidney function, which comprises administering to the mammal an effective disease-treating or condition-treating amount of a compound according to Formula (I) having the structure:

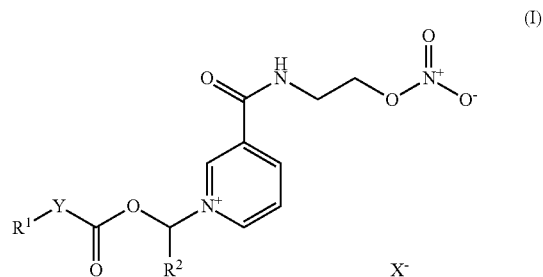

or a pharmaceutical composition thereof;
wherein $X^-$ is a counter ion; Y is —C(H)$_2$—, —O—, or —N(R$^3$)—;
R$^1$ is substituted or unsubstituted C$_1$-C$_4$ alkyl, substituted or unsubstituted C$_3$-C$_7$-cycloalkyl, or substituted or unsubstituted 4-7 membered heterocycloalkyl;

$R^2$ is H or $C_1$-$C_4$ alkyl; and $R^3$ is H or substituted or unsubstituted $C_1$-$C_4$ alkyl; or $R^1$ and $R^3$ are joined together to form a 4-7 membered substituted or unsubstituted heterocycloalkyl.

In some embodiments, the present invention provides use of a compound according to Formula (I) having the structure:

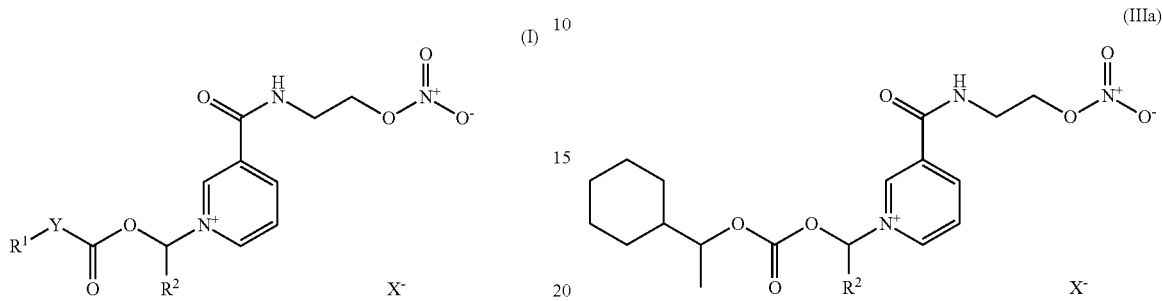

(I)

in a treatment of a disease or a condition related to kidney;
wherein $X^-$ is a counter ion; Y is —C(H)$_2$—, —O—, or —N($R^3$)—;

$R^1$ is substituted or unsubstituted $C_1$-$C_4$ alkyl, substituted or unsubstituted $C_3$-$C_7$-cycloalkyl, or substituted or unsubstituted 4-7 membered heterocycloalkyl;

$R^2$ is H or $C_1$-$C_4$ alkyl; and $R^3$ is H or substituted or unsubstituted $C_1$-$C_4$ alkyl; or $R^1$ and $R^3$ are joined together to form a 4-7 membered substituted or unsubstituted heterocycloalkyl.

In some embodiments, Y is —C(H)$_2$—. In some embodiments, Y is —O—. In some embodiments, Y is —N($R^3$)—. In particular embodiments, Y is —N(H)—.

In some embodiments, $R^2$ is H, Me, Et, or i-Pr. In a particular embodiment, $R^2$ is H.

In some embodiments, $R^1$ is ethyl substituted with cyclohexyl.

In some embodiments, $R^1$ is 2-cyclohexyl-ethyl.

In some embodiments, the disease or condition is Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome.

In a particular embodiment, the disease or condition is Contrast Induced Nephropathy.

In a particular embodiment, the disease or condition is Tenofovir induced AKI.

In a particular embodiment, the disease or condition is Aminoglycosides induced AKI.

In a particular embodiment, the disease or condition is AKI after surgery.

In a particular embodiment, the disease or condition is AKI in patients with Dialysis.

In a particular embodiment, the disease or condition is Diabetic Nephropathy.

In a more particular embodiment, the disease or condition is chronic kidney disease or CKD.

In some embodiments, the compound is:

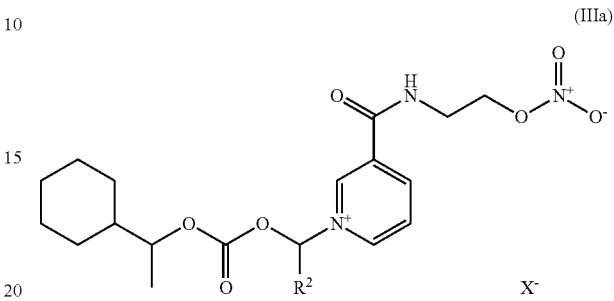

(IIIa)

wherein $X^-$ and $R^2$ are as described for formula (I) herein.
In some embodiments, the compound is:

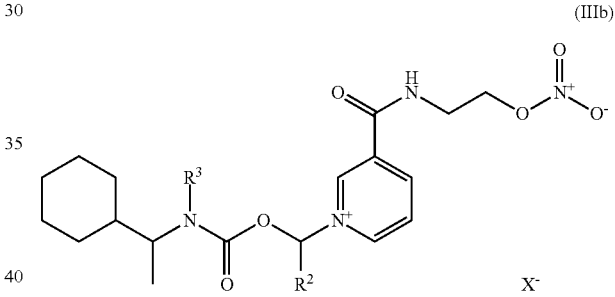

(IIIb)

wherein $X^-$ and $R^2$ are as described for formula (I) herein.

In some embodiments, with respect to formula (IIIa) or (IIIb), $R^2$ is H or Me. In some embodiments, $R^3$ is H, Me, Et, or i-Pr. In particular embodiments, each $R^2$ and $R^3$ is H.

In some embodiments, with respect to formula (IIIa) or (IIIb), the compound is an R-isomer. In some embodiments, with respect to formula (IIIa) or (IIIb), the compound is an S-isomer.

In some embodiments, the compound is:

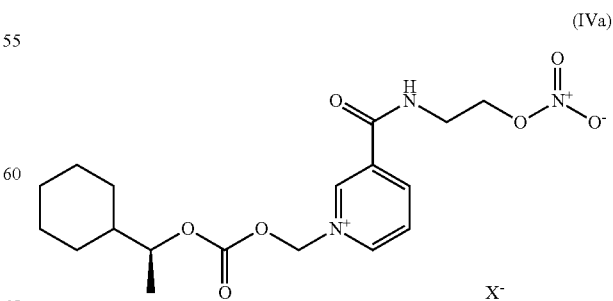

(IVa)

wherein $X^-$ is as described for formula (I) herein.

In some embodiments, the compound is:

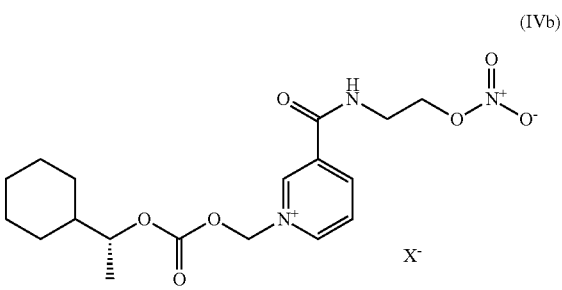

(IVb)

wherein X⁻ is as described for formula (I) herein.

In some embodiments, the compound is:

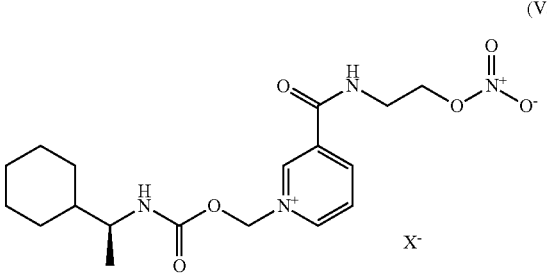

(Va)

wherein X⁻ is as described for formula (I) herein.

In some embodiments, the compound is:

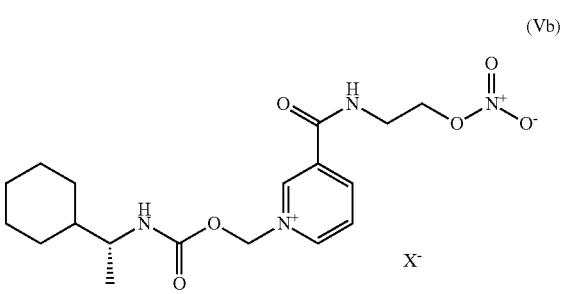

(Vb)

wherein X⁻ is as described for formula (I) herein.

In some embodiments, X⁻ is Cl⁻. In another embodiment, X⁻ is Br⁻. In another embodiment, X⁻ is I⁻. In another embodiment, X⁻ is F⁻. In another embodiment, X⁻ is MeSO₂O⁻.

In some embodiments, the present invention provides pharmaceutical compositions comprising a therapeutically effective amount of a compound of formula (I) and a pharmaceutically acceptable excipient. In some embodiments, the pharmaceutical composition comprising the compound of formula (I) is formulated for a route of administration selected from oral administration, parenteral administration, buccal administration, nasal administration, topical administration, or rectal administration. In some embodiments, the present invention provides methods for treating a disease or condition comprising administering to a patient in need a therapeutically effective amount of a compound of formula (I). In some embodiments the disease is selected from Chronic Kidney Disease (CKD), Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome. In some embodiments, the present invention provides a method for treating a CKD disease or condition comprising administering to a patient in need a therapeutically effective amount of a compound of formula (I). In some embodiments, the disease is diabetic nephropathy. In some embodiments, the disease or condition is acute kidney failure (AKI).

In some embodiments the disease or condition is acute kidney failure and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome.

In some embodiments, the present invention provides a method for treating Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome comprising administering to a patient in need a therapeutically effective amount of a compound of Formula (I).

It is understood that one of ordinary skill in the art to provide compounds that are chemically stable and that can be synthesized by techniques known in the art, as well as those set forth herein.

In some embodiments, the present invention provides pharmaceutical compositions, which include a therapeutically effective amount of at least one of any of the compounds herein, or a pharmaceutically acceptable salt, pharmaceutically active metabolite, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are kidney related, are provided. The effective amounts and concentrations are effective for ameliorating any of the symptoms of any of the diseases, disorders or conditions disclosed herein.

In certain embodiments, provided herein is a pharmaceutical composition containing: i) a physiologically acceptable carrier, diluent, and/or excipient; and ii) one or more compounds provided herein.

In some embodiments, provided herein are methods for treating a patient of treating a disease, disorder, or condition, which related to kidney, in a patient, which includes administering to the patient a therapeutically effective amount of at least one of any of the compounds herein, or pharmaceutically acceptable salt, pharmaceutically active metabolite, pharmaceutically acceptable prodrug, or pharmaceutically acceptable solvate.

In some embodiments, compounds provided herein are administered to a human.

In some embodiments, compounds provided herein are orally administered.

In some embodiments, compounds provided herein are used for the formulation of a medicament for treating a disease, disorder, or condition, which is related to kidney. In some embodiments, compounds provided herein are used for the formulation of a medicament for kidney disease or condition.

Articles of manufacture including packaging material, a compound or composition or pharmaceutically acceptable derivative thereof provided herein, which is effective for treating the kidney disease or condition, within the packaging material, and a label that indicates that the compound or composition, or pharmaceutically acceptable salt, pharmaceutically active metabolite, pharmaceutically acceptable prodrug, or pharmaceutically acceptable solvate thereof, is used for treating the kidney disease or condition, are provided.

In some embodiments, provided herein is a method for treating the kidney disease or condition in a subject in need thereof by administering to the subject thereof a composition containing a therapeutically effective amount of at least one compound having the structure of formula (I). In some embodiments, the subject in need is suffering from Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome.

In some embodiments, the subject in need is suffering from a kidney condition or disease, e.g., Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome.

In some embodiments, provided herein is a method for treating the kidney disease or condition by administering to a subject in need thereof a composition containing a therapeutically effective amount of at least one compound having the structure of Formula (I)-(Vb). In some embodiments, kidney disease or condition is Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome.

In any of the aforementioned embodiments are some embodiments in which administration is enteral, parenteral, or both, and wherein (a) an effective amount of a provided compound is systemically administered to the mammal; (b) an effective amount of a provided compound is administered orally to the mammal; (c) an effective amount of a provided compound is intravenously administered to the mammal; (d) an effective amount of a provided compound is administered by inhalation; (e) an effective amount of a provided compound is administered by nasal administration; or (f) an effective amount of a provided compound is administered by injection to the mammal; (g) an effective amount of a provided compound is administered topically (dermal) to the mammal; (h) an effective amount of a provided compound is administered by ophthalmic administration; or (i) an effective amount of a provided compound is administered rectally to the mammal.

In any of the aforementioned embodiments are some embodiments comprising single administrations of an effective amount of a provided compound including some embodiments in which (i) a provided compound is administered once; (ii) a provided compound is administered to the mammal multiple times over the span of one day; (iii) continually; or (iv) continuously.

In any of the aforementioned embodiments are some embodiments comprising multiple administrations of an effective amount of a provided compound, including some embodiments in which (i) a provided compound is administered in a single dose; (ii) the time between multiple administrations is every 6 hours; (iii) a provided compound is administered to the mammal every 8 hours. In some embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

DETAILED DESCRIPTION OF THE INVENTION

Certain Terminology

Figure 1:
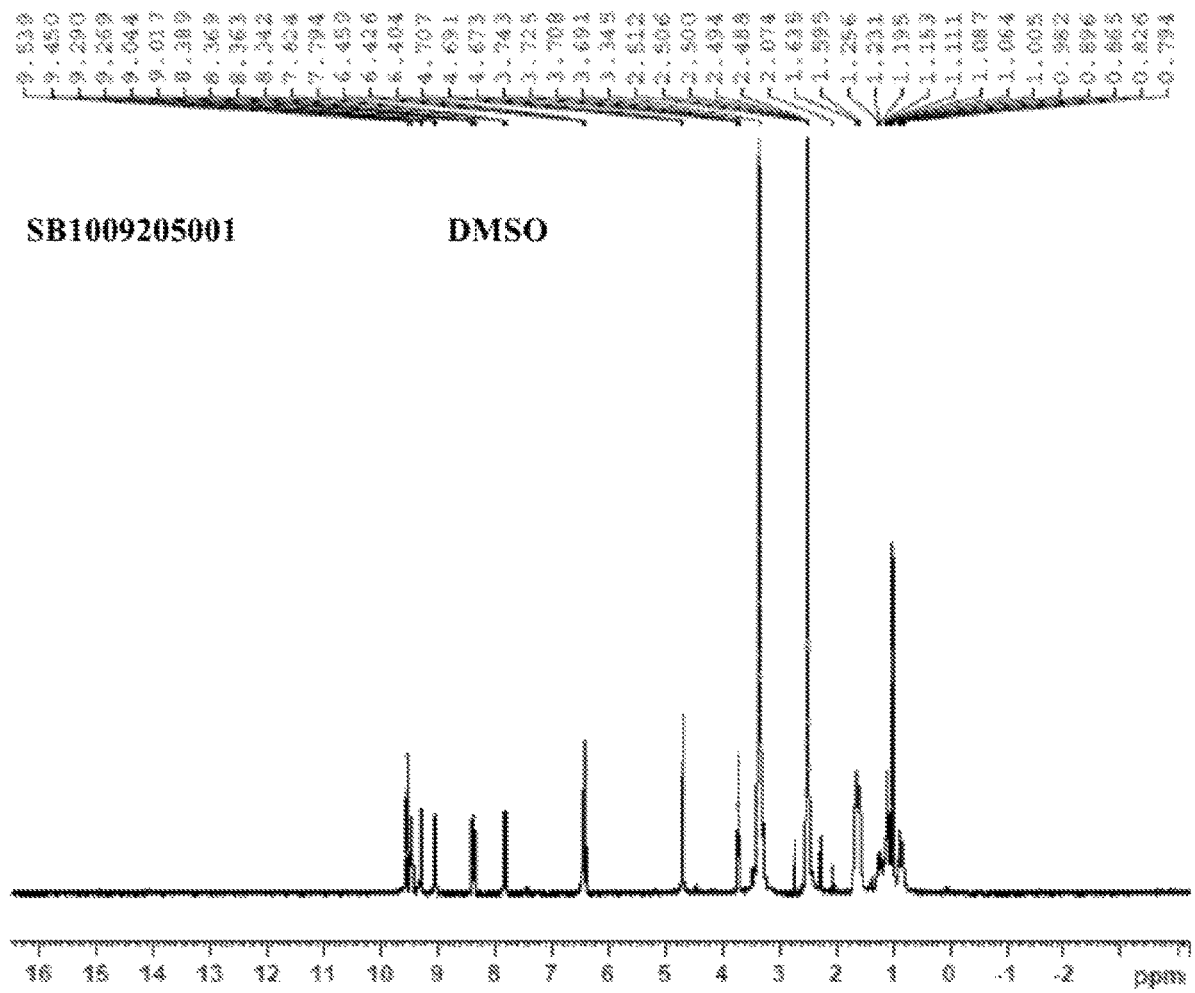
FIG. 1 shows $^1$H NMR of Compound A in DMSO-d6.
Figure 2:
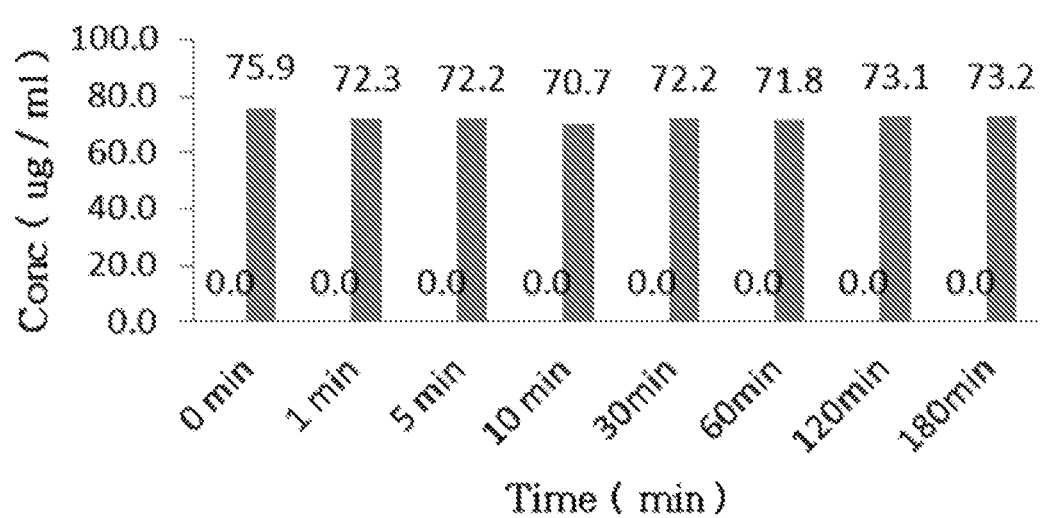
FIG. 2 shows conversion of Compound A to nicorandil in rat plasma at various time points. Complete conversion to nicorandil was observed with no trace of Compound A.

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. Use of the term "including" as well as other forms, such as "include", "includes," and "included," is not limiting. Definition of standard chemistry terms may be found in reference works, including Carey and Sundberg "Advanced Organic Chemistry 4$^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In some embodiments, an alkyl comprises five to fifteen carbon atoms (e.g., $C_5$-$C_{15}$ alkyl). In certain embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl (n-pr), 1-methylethyl (iso-propyl or i-Pr), n-butyl (n-Bu), n-pentyl, 1,1-dimethylethyl (t-butyl, or t-Bu), 3-methylhexyl, 2-methylhexyl, and the like. Unless stated otherwise specifically in the specification, an alkyl group is optionally substituted as defined and described below and herein.

The alkyl group could also be a "lower alkyl" having 1 to 6 carbon atoms.

As used herein, $C_1$-$C_x$ includes $C_1$-$C_2$, $C_1$-$C_3$ ... $C_1$-$C_x$.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In some embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted as defined and described below and herein.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In some embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted as defined and described below and herein.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted as defined and described below and herein.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted as defined and described below and herein. "Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl (Ph), fluorenyl, and naphthyl. Unless stated otherwise specifically in the specification, the term "aryl" or the prefix "ar-" (such as in "aralkyl") is meant to include aryl radicals optionally substituted as defined and described below and herein.

"Aralkyl" refers to a radical of the formula —$R^c$-aryl where $R^C$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In some embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted as defined and described below and herein. "Halo" or "halogen" refers to bromo, chloro, fluoro or iodo substituents.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In some embodiments in which two or more hydrogen atoms are replaced with halogen atoms, the halogen atoms are not all the same as one another.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three to 14 ring atoms, such as three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

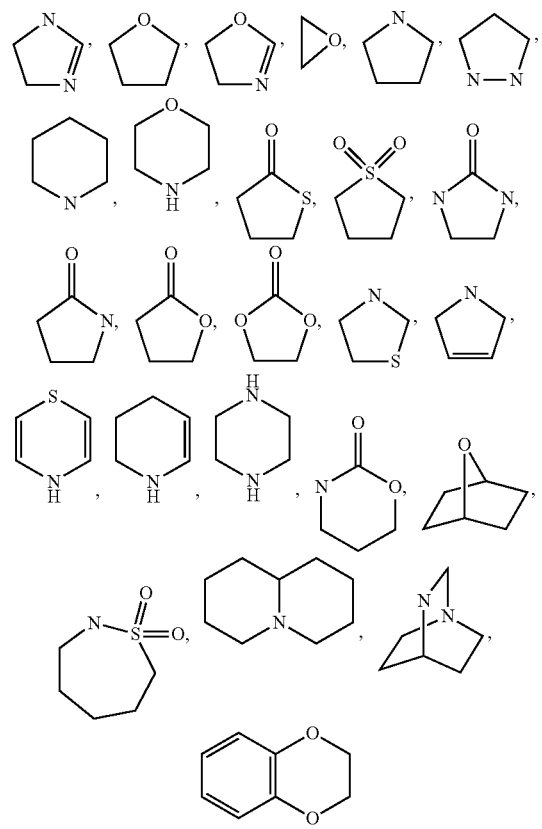

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In some embodiments, heteroaryl rings have five, six, seven, eight, nine, or more than nine ring atoms. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted as defined and described below and herein.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Sulfanyl" refers to the —S— radical.
"Sulfinyl" refers to the —S(=O)— radical.
"Sulfonyl" refers to the —S(=O)$_2$— radical.
"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.

An "alkoxy" group refers to a (alkyl)O— group, where alkyl is as defined herein.

An "aryloxy" group refers to an (aryl)O— group, where aryl is as defined herein.

"Carbocyclylalkyl" means an alkyl radical, as defined herein, substituted with a carbocyclyl group. "Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond," "direct bond" or "single bond" refers to a chemical bond between two atoms, or two moieties when the atoms joined by the bond are considered to be part of larger substructure.

An "isocyanato" group refers to a —NCO group.
An "isothiocyanato" group refers to a —NCS group.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "alkylthioalkyl" group refers to an alkyl group substituted with a —S-alkyl group.

As used herein, the term "acyloxy" refers to a group of formula RC(=O)O—.

"Carboxy" means a —C(O)OH radical.

As used herein, the term "acetyl" refers to a group of formula —C(=O)CH$_3$.

"Acyl" refers to the group —C(O)R.

As used herein, the term "trihalomethanesulfonyl" refers to a group of formula X$_3$CS(=O)$_2$— where Y is a halogen.

"Cyanoalkyl" means an alkyl radical, as defined herein, substituted with at least one cyano group.

As used herein, the term "N-sulfonamido" or "sulfonylamino" refers to a group of formula RS(=O)$_2$NH—.

As used herein, the term "O-carbamyl" refers to a group of formula —OC(=O)NR$_2$.

As used herein, the term "N-carbamyl" refers to a group of formula ROC(=O)NH—.

As used herein, the term "O-thiocarbamyl" refers to a group of formula —OC(=S)NR$_2$.

As used herein, "N-thiocarbamyl" refers to a group of formula ROC(=S)NH—.

As used herein, the term "C-amido" refers to a group of formula —C(=O)NR$_2$.

"Aminocarbonyl" refers to a —CONH$_2$ radical.

As used herein, the term "N-amido" refers to a group of formula RC(=O)NH—.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

As described herein, compounds of the invention may be "optionally substituted". In general, the term "substituted," whether preceded by the term "optionally" or not, means that one or more hydrogens of a designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, [SC(S)SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —(CH$_2$)$_{0-4}$OC(O)NR$^\circ$2; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$;

—(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rf are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "nucleophile" or "nucleophilic" refers to an electron rich compound, or moiety thereof.

The term "electrophile", or "electrophilic" refers to an electron poor or electron deficient molecule, or moiety thereof. Examples of electrophiles include, but in no way are limited to, Michael acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (I)-(Vb) dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which compounds disclosed herein, such as, compounds of any of Formula ((I)-(Vb) are absorbed into the general circulation when the pharmaceutical composition is taken orally as compared to intravenous injection.

"Blood plasma concentration" refers to the concentration of compounds disclosed herein, such as, compounds of any of Formula (I)-(Vb) in the plasma component of blood of a subject. It is understood that the plasma concentration of compounds of any of Formula (I)-(Vb) may vary significantly between subjects, due to variability with respect to metabolism and/or possible interactions with other therapeutic agents. In accordance with some embodiments disclosed herein, the blood plasma concentration of the compounds of any of Formula (I)-(Vb) may vary from subject to subject. Likewise, values such as maximum plasma concentration (C$_{max}$) or time to reach maximum plasma concentration (T$_{max}$), or total area under the plasma concentration time curve (AUC$_{(0-\infty)}$) may vary from subject to subject. Due to this variability, the amount necessary to constitute "a therapeutically effective amount" of a compound of any of Formula (I)-(Vb) may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (I)-(Vb), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient that will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

As used herein, the term "selective binding compound" refers to a compound that selectively binds to any portion of one or more target proteins.

As used herein, the term "selectively binds" refers to the ability of a selective binding compound to bind to a target protein, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulater refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" or "patient" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Methods described herein include administering to a subject in need a composition containing a therapeutically effective amount of one or more compounds described herein.

A number of animal models of are useful for establishing a range of therapeutically effective doses of pyridyl compounds for treating any of the foregoing diseases.

For example, dosing of pyridyl compounds for treating a kidney disease can be assessed in a rat models as described herein.

The therapeutic efficacy of a provided compound for one of the foregoing diseases can be optimized during a course of treatment.

Compounds

In the following description of pyridyl compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

Pyridyl compounds can be used for the manufacture of a medicament for treating any of the foregoing conditions Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome.

Described herein are compounds of any of Formulae (I)-(Vb). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (I)-(Vb) are also provided.

In some embodiments, provided herein are pyridyl according to compounds of formula (I).

In some embodiments, the present invention provides a compound according to formula (I) having the structure:

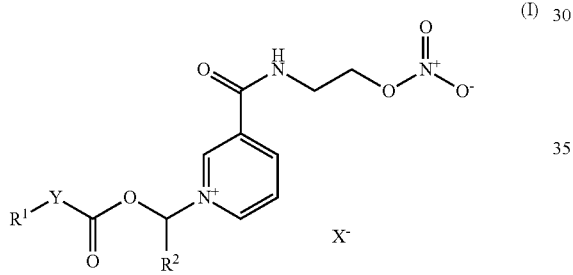

(I)

or a pharmaceutical composition thereof;
wherein $X^-$ is a counter ion; Y is —C(H)$_2$—, —O—, or —N(R$^3$)—;
R$^1$ is substituted or unsubstituted C$_1$-C$_4$ alkyl, substituted or unsubstituted C$_3$-C$_7$-cycloalkyl, or substituted or unsubstituted 4-7 membered heterocycloalkyl;
R$^2$ is H or C$_1$-C$_4$ alkyl; and
R$^3$ is H or substituted or unsubstituted C$_1$-C$_4$ alkyl; or R$^1$ and R$^3$ are joined together to form a 4-7 membered substituted or unsubstituted heterocycloalkyl.

In some embodiments, provided herein are uses of a compound according to formula (I):

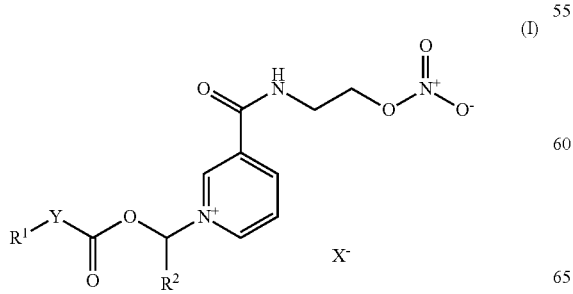

(I)

in a treatment of a disease or a condition related to kidney;
wherein $X^-$ is a counter ion; Y is —C(H)$_2$—, —O—, or —N(R$^3$)—;
R$^1$ is substituted or unsubstituted C$_1$-C$_4$ alkyl, substituted or unsubstituted C$_3$-C$_7$-cycloalkyl, or substituted or unsubstituted 4-7 membered heterocycloalkyl;
R$^2$ is H or C$_1$-C$_4$ alkyl; and
R$^3$ is H or substituted or unsubstituted C$_1$-C$_4$ alkyl; or R$^1$ and R$^3$ are joined together to form a 4-7 membered substituted or unsubstituted heterocycloalkyl.

In some embodiments, R$^2$ is H, Me, Et, or i-Pr.
In some embodiments, R$^2$ is H.
In some embodiments, Y is —C(H)$_2$—.
In some embodiments, Y is —O—.
In some embodiments, Y is —N(R$^3$)—.

In some embodiments, the compound is according to formula (IIa), (IIb), or (IIc):

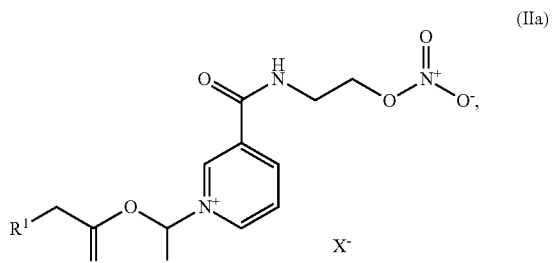

(IIa)

(IIb)

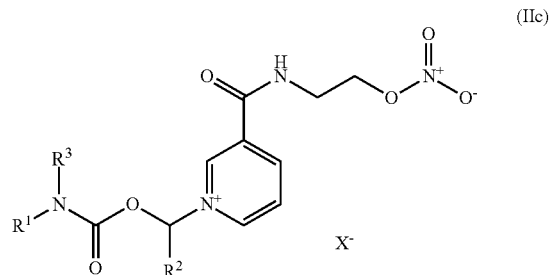

(IIc)

wherein
$X^-$ is a counter ion;
R$^1$ is substituted or unsubstituted C$_1$-C$_4$ alkyl, substituted or unsubstituted C$_3$-C$_7$-cycloalkyl, or substituted or unsubstituted 4-7 membered heterocycloalkyl;
R$^2$ is H or C$_1$-C$_4$ alkyl; and
R$^3$ is H or substituted or unsubstituted C$_1$-C$_4$ alkyl; or R$^1$ and R$^3$ are joined together to form a 4-7 membered substituted or unsubstituted heterocycloalkyl.

In some embodiments, R$^1$ is substituted or unsubstituted C$_1$-C$_4$ alkyl.
In some embodiments, R$^1$ is C$_1$-C$_4$ alkyl, unsubstituted or substituted with C$_3$-C$_7$ cycloalkyl.

In some embodiments, $R^1$ is Me, Et, i-Pr, n-Pr, n-Bu, i-Bu, sec-Bu, or t-Bu.

In some embodiments, $R^1$ is Me or Et substituted with cyclopropyl, cyclobutyl, cyclopentyl or cyclohexyl.

In some embodiments, $R^1$ is $C_3$-$C_7$-cycloalkyl unsubstituted or substituted with Me or Et.

In some embodiments, $R^1$ is cyclopropyl, cyclobutyl, cyclopentyl or cyclohexyl.

In some embodiments, $R^3$ is H or substituted or unsubstituted $C_1$-$C_4$ alkyl.

In some embodiments, $R^3$ is H.

In some embodiments, $R^3$ is Me, Et, i-Pr, n-Pr, n-Bu, i-Bu, sec-Bu, or t-Bu.

In some embodiments, $R^1$ and $R^3$ are joined together to form a 4-7 membered substituted or unsubstituted heterocycloalkyl.

In some embodiments, $R^1$ and $R^3$ are joined together to form pyrrolidinyl, piperidinyl, or morpholinyl.

In some embodiments, the compound is according to formula (IIIa), or (IIIb):

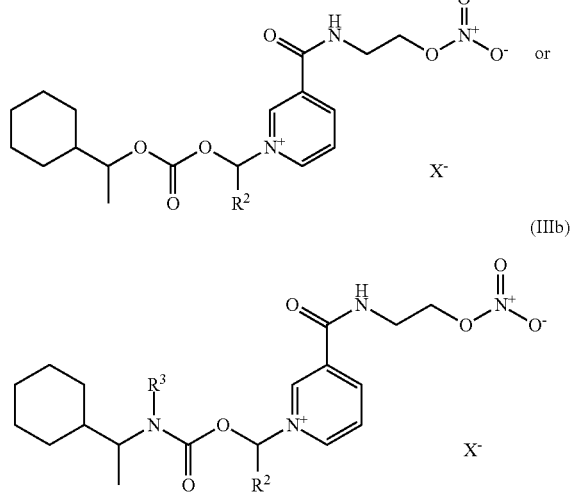

wherein
$X^-$ is a counter ion;
$R^2$ is H or $C_1$-$C_4$ alkyl; and
$R^3$ is H or substituted or unsubstituted $C_1$-$C_4$ alkyl.

In some embodiments, $R^3$ is H, Me, Et, or i-Pr.

In some embodiments, $R^3$ is H.

In some embodiments, $R^2$ is H or Me.

In some particular embodiments, the compound is according to formula (IIIb); and each $R^2$ and $R^3$ is H.

In some embodiments, the compound is according to formula (IVa), or (IVb):

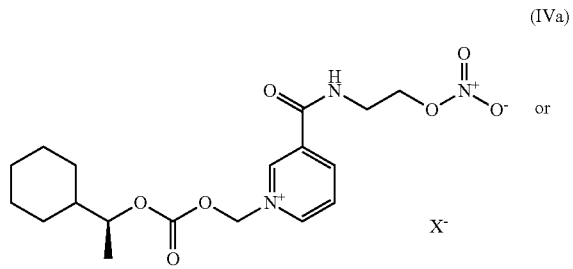

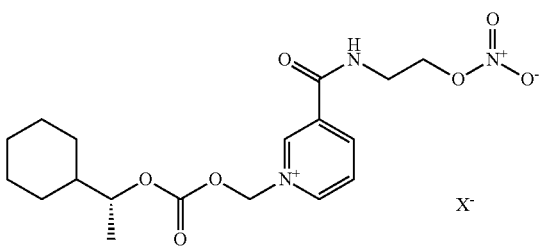

wherein $X^-$ is a counter ion.

In some embodiments, the compound is according to formula (Va), or (Vb):

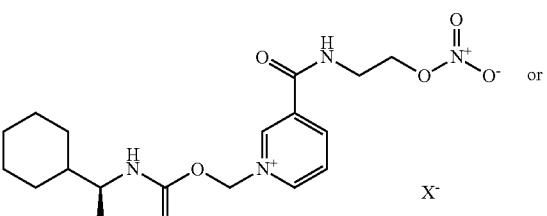

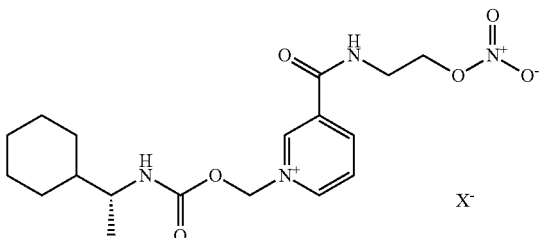

wherein $X^-$ is a counter ion.

In some embodiments, the counter ion is any pharmaceutically acceptable anion. In some embodiment, the counter ion is a halide or a sulfonate. In a particular embodiment, the counter ion is $F^-$, $Cl^-$, $Br^-$, $I^-$. In another particular embodiment, the counter ion is benzene sulfonate or methyl sulfonate.

In some embodiments, $X^-$ is $F^-$, $Cl^-$, $Br^-$, $I^-$, or $MeSO_2O^-$.

In a particular embodiment, $X^-$ is $Cl^-$, or $I^-$. In a more particular embodiment, $X^-$ is $I^-$.

In some embodiments, the present invention provides, a pharmaceutical composition comprising a compound according to formula (I).

In some embodiments, the present invention provides, a pharmaceutical composition comprising a therapeutically effective amount of a compound of formula (I), and a pharmaceutically acceptable excipient.

In some embodiments, the pharmaceutical composition is formulated for a route of administration selected from oral administration, parenteral administration, buccal administration, nasal administration, topical administration, or rectal administration.

In some embodiments, the present invention provides, methods for treating a kidney disease or condition comprising administering to a patient in need the pharmaceutical composition of the present invention.

In some embodiments, the kidney disease is selected from Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome.

In a particular embodiment, the disease or condition is Contrast Induced Nephropathy.

In a particular embodiment, the disease or condition is Tenofovir induced AKI.

In a particular embodiment, the disease or condition is Aminoglycosides induced AKI.

In a particular embodiment, the disease or condition is AKI after surgery.

In a particular embodiment, the disease or condition is AKI in patients with Dialysis.

In a particular embodiment, the disease or condition is Diabetic Nephropathy.

In a more particular embodiment, the disease or condition is chronic kidney disease or CKD.

In some embodiments, the disease or condition is:

| ACUTE | CHRONIC |
|---|---|
| Acute Kidney Injury (AKI) | Chronic Kidney Disease (CKD) |
| Acute tubular necrosis | IgA Nephropathy |
| Transplant related Ischemia | Diabetic Nephropathy |

In some embodiments, the disease or condition is:

| ACUTE KIDNEY INJURY DISEASE | | |
|---|---|---|
| Drug Induced AKI | Post Surgery/Transplant | Other causes of AKI |
| Cisplatin induced AKI in patients with Head and Neck Cancer | AKI after surgery for partial nephrectomy | Cirrhosis |
| Aminoglycosides induced AKI in patients with Cystic Fibrosis | AKI post Kidney transplant | Hepatorenal syndrome |
| Tenofovir induced AKI in patients with Hep B and HIV | AKI for patients under dialysis | Sepsis |
| Contrast induced AKI | | |

In some embodiments, the compound is according to formula (Va).

In some embodiments, the compound is according to formula (Vb).

In some embodiments, the present invention provides, a pharmaceutical composition comprising a pharmaceutically acceptable carrier and a pharmaceutically effective amount of a compound according to any one of the formulas described herein. In some embodiments, the compound is according to any one of Formula (I)-(Vb).

In some embodiments, the pharmaceutical composition is formulated for a route of administration selected from oral administration, parenteral administration, buccal administration, nasal administration, topical administration, or rectal administration.

In some embodiments, the carrier is a parenteral carrier.
In some embodiments, the carrier is an oral carrier.
In some embodiments, the carrier is a topical carrier.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Throughout the specification, groups and substituents thereof can be chosen by one skilled in the field to provide stable moieties and compounds.

In some embodiments, the compounds of formula (I)-(Vb) are used to treat patients suffering from kidney conditions or diseases, including, but not limited to, Chronic Kidney Disease, Diabetic Nephropathy, IgA Nephropathy, Acute Kidney Failure, Acute tubular necrosis, Transplant related Ischemia, Acute Kidney Disease and types of AKI such as Cisplatin induced AKI, Aminoglycosides induced AKI, Tenofovir induced AKI, Contrast Induced Nephropathy, AKI after surgery for partial nephrectomy, AKI post kidney transplant, AKI in patients with Dialysis, AKI after Cardiac surgery, AKI in patients inside ICU, AKI caused by Cirrhosis or Sepsis and AKI caused by hepatorenal syndrome and other diseases.

Preparation of Compounds

Compounds of any of Formula (I)-(Vb) may be synthesized using synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wisconsin), Bachem (Torrance, California), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Additional methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

In some embodiments, representative compounds of Formula (I) are prepared according to synthetic schemes and methods described in a US patent to Dugar et al., U.S. Pat. No. 9,359,376.

Further Forms of Compounds

Compounds disclosed herein have a structure of Formula (I)-(Vb). It is understood that when reference is made to compounds described herein, it is meant to include compounds of any of Formula (I), (IIa)-(IIc), (IIIa)-(IIIb), (IVa)-(IVb), or (Va)-(Vb) as well as to all of the specific compounds that fall within the scope of these generic formulae, unless otherwise indicated.

Compounds described herein may possess one or more stereocenters and each center may exist in the R or S configuration. Compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diastereomeric mixtures can be separated into their individual diastereomers on the basis of their physical chemical differences by methods known, for example, by chromatography and/or fractional crystallization. In some embodiments, enantiomers can be separated by chiral chromatographic columns. In some embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

Methods and formulations described herein include the use of N-oxides, crystalline forms, or pharmaceutically acceptable salts of compounds described herein, as well as active metabolites of these compounds having the same type of activity. In some situations, compounds may exist as tautomers. All tautomers are included within the scope of the compounds presented herein. In addition, compounds described herein can exist in unsolvated as well as solvated forms with pharmaceutically acceptable solvents such as water, ethanol, and the like. Solvated forms of compounds presented herein are also considered to be disclosed herein.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

The salts are recovered by using at least one of the following techniques: filtration, precipitation with a non-solvent followed by filtration, evaporation of the solvent, or, in the case of aqueous solutions, lyophilization.

Throughout the specification, groups and substituents thereof can be chosen by one skilled in the field to provide stable moieties and compounds.

Pharmaceutical Composition/Formulation

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of a compound described herein, such as, for example, compounds of any of Formula (I)-(Vb) with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical compositions described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical compositions described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any of (I)-(Vb) as an active ingredient in free-acid or free-base form, or in a pharmaceutically acceptable salt form. In addition, the methods and pharmaceutical compositions described herein include the use of N-oxides, crystalline forms, as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.10% to about 10% w/v methionine, (c) about 0.10% to about 2% w/v monothioglycerol, (d) about 1 mM to about 10 mM EDTA, (e) about 0.010% to about 2% w/v ascorbic acid, (f) 0.003% to about 0.02% w/v polysorbate 80, (g) 0.0010% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of any of Formula (I)-(Vb) and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet®

Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, µg, or ng of therapeutic agent per ml, dl, or 1 of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any of Formula (I)-(Vb) can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In some embodiments, the pharmaceutical composition is in the form of a powder. In some embodiments, the pharmaceutical composition is in the form of a tablet, including but not limited to, a fast-melt tablet. Additionally, pharmaceutical compositions described herein may be administered as a single capsule or in multiple capsule dosage form. In some embodiments, the pharmaceutical composition is administered in two, or three, or four, capsules or tablets.

In some embodiments, solid dosage forms, e.g., tablets, effervescent tablets, and capsules, are prepared by mixing particles of a compound of any of Formula (I)-(Vb) with one or more pharmaceutical excipients to form a bulk blend composition. When referring to these bulk blend compositions as homogeneous, it is meant that the particles of the compound of any of Formula (I)-(Vb) are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some embodiments, using standard coating procedures, such as those described in Remington's Pharmaceutical Sciences, 20th Edition (2000), a film coating is provided around the formulation of the compound of any of Formula (I)-(Vb). In some embodiments, some or all of the particles of the compound of any of Formula (I)-(Vb) are coated. In some embodiments, some or all of the particles of the compound of any of Formula (I)-(Vb), are microencapsulated. In still some embodiments, the particles of the compound of any of Formula (I)-(Vb) are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (I)-(Vb) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

t should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In some embodiments, one or more layers of the pharmaceutical composition are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In some embodiments, the compressed tablets will include a film surrounding the final compressed tablet. In some embodiments, the film coating can provide a delayed release of the compound of any of Formula (I)-(Vb) from the formulation. In some embodiments, the film coating aids in patient compliance (e.g., Opadry® coatings or sugar coating). Film coatings including Opadry® typically range from about 1% to about 3% of the tablet weight. In some embodiments, the compressed tablets include one or more excipients.

A capsule may be prepared, for example, by placing the bulk blend of the formulation of the compound of any of Formula (I)-(Vb), described above, inside of a capsule. In some embodiments, the formulations (non-aqueous suspensions and solutions) are placed in a soft gelatin capsule. In some embodiments, the formulations are placed in standard gelatin capsules or non-gelatin capsules such as capsules comprising HPMC. In some embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula (I)-(Vb) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In some embodiments, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula (I)-(Vb) which sufficiently isolate the compound of any of (I)-(Vb) from other non-compatible excipients. Materials compatible with compounds of any of Formula (I)-(Vb) are those that delay the release of the compounds of any of Formula (I)-(Vb), in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In some embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In some embodiments, the microencapsulating material useful for delaying the release of the pharmaceutical compositions is from the USP or the National Formulary (NF). In some embodiments, the microencapsulation material is Klucel. In some embodiments, the microencapsulation material is methocel.

Microencapsulated compounds of any of Formula (I)-(Vb) may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In some embodiments, the particles of compounds of any of Formula (I)-(Vb) are microencapsulated prior to being formulated into one of the above forms. In still some embodiments, some or most of the particles are coated prior to being further formulated by using standard coating procedures, such as those described in Remington's Pharmaceutical Sciences, 20th Edition (2000).

In some embodiments, the solid dosage formulations of the compounds of any of Formula (I)-(Vb) are plasticized (coated) with one or more layers. Illustratively, a plasticizer is generally a high boiling point solid or liquid. Suitable plasticizers can be added from about 0.010% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In some embodiments, a powder including the formulations with a compound of any of Formula (I)-(Vb), described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still some embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the formulations described herein, which include a compound of Formula (I), are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In some embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

The pharmaceutical solid oral dosage forms including formulations described herein, which include a compound of any of (I)-(Vb) can be further formulated to provide a controlled release of the compound of Formula (I). Controlled release refers to the release of the compound of any of Formula (I)-(Vb) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In some embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP pseudolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In some embodiments, the formulations described herein, which include a compound of Formula (I), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formula (I)-(Vb) may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference. In some embodiments, the controlled release dosage form is pulsatile release solid oral dosage form including at least two groups of particles, (i.e. multiparticulate) each containing the formulation described herein. The first group of particles provides a substantially immediate dose of the compound of any of (I)-(Vb) upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any of Formula (I)-(Vb) in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any of Formula (I).

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical compositions are provided that include particles of the compounds of any of Formula (I)-(Vb), described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition to the particles of compound of Formula (A), the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In some embodiments, an aqueous suspension can be re-suspended into a homogenous suspension by physical agitation lasting less than 1 minute. In some embodiments, an aqueous suspension can be re-suspended into a homogenous suspension by physical agitation lasting less than 45 seconds. In yet some embodiments, an aqueous suspension can be re-suspended into a homogenous suspension by physical agitation lasting less than 30 seconds. In still some embodiments, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In some embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In some embodiments, the aqueous liquid dispersion can comprise a sweetening agent or flavoring agent in a concentration ranging from about 0.0010% to about 1.0% the volume of the aqueous dispersion. In some embodiments, the aqueous liquid dispersion can comprise a sweetening agent or flavoring agent in a concentration ranging from about 0.005% to about 0.5% the volume of the aqueous dispersion. In yet some embodiments, the aqueous liquid dispersion can comprise a sweetening agent or flavoring agent in a concentration ranging from about 0.010% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical compositions described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

t is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116, 817 and 6,391,452, each of which is specifically incorporated by reference. Formulations that include a compound of any of Formula (I)-(Vb) which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula (I)-(Vb), described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations that include compounds of any of Formula (I)-(Vb) may be administered using a variety of formulations known in the art. For example, such formulations include, but are not limited to, U.S. Pat. Nos. 4,229, 447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula (I)-(Vb), is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any of Formula (I)-(Vb), and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In some embodiments, the transdermal formulations described herein include at least three components: (1) a formulation of a compound of any of Formula (I); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In some embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formula (I)-(Vb). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of any of Formula (I)-(Vb), suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The compounds described herein can be used in the preparation of medicaments for the treatment of diseases or conditions related to kidney. In addition, a method for treating any of the diseases or conditions described herein in a subject in need of such treatment, involves administration of pharmaceutical compositions containing at least one compound of any of Formula (I)-(Vb), described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by using the compounds of the invention.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

The examples below as well as throughout the application, the following abbreviations have the following meanings. If not defined, the terms have their generally accepted meanings.

aq=aqueous
Boc=tert-butyloxycarbonyl
t-BuOH=tertiary butanol
DCE=1,2-dichloroethane
DCM=dichloromethane
DIAD=diisopropyl azodicarboxylate
DIEA or DIPEA=N,N-diisopropylethylamine
DMAP=dimethylaminopyridine
DMF=dimethylformamide
DMSO=dimethylsulfoxide
ESI=electron spray ionization
EA=ethyl acetate
g=gram
HCl=hydrogen chloride
HPLC=high performance liquid chromatography
hr=hour
$^1$H NMR=proton nuclear magnetic resonance
IPA=isopropyl alcohol
KOAc=potassium acetate
LC-MS=liquid chromatography mass spectroscopy
M=molar
MeCN=acetonitrile
MeOH=methanol
mg=milligram
min=minute
ml=milliliter
mM=millimolar
mmol=millimole
m.p.=melting point
MS=mass spectrometry
m/z=mass-to-charge ratio
N=normal
NIS=N-iodosuccinimide
nM=nanomolar
nm=nanometer
Pd(dppf)Cl$_2$=[1,1'-Bis(diphenylphosphino)ferrocene]dichloropalladium(II)
PE=petroleum ether
PyBOP=benzotriazol-1-yl-oxytripyrrolidinophosphonium hexafluorophosphate
quant.=quantitative
RP=reverse phase
RT, rt or r.t.=room temperature
Sat.=saturated
TEA=triethylamine
TFA=trifluoroacetic acid
µL=microliter
µM=micromolar Generic Synthetic Scheme

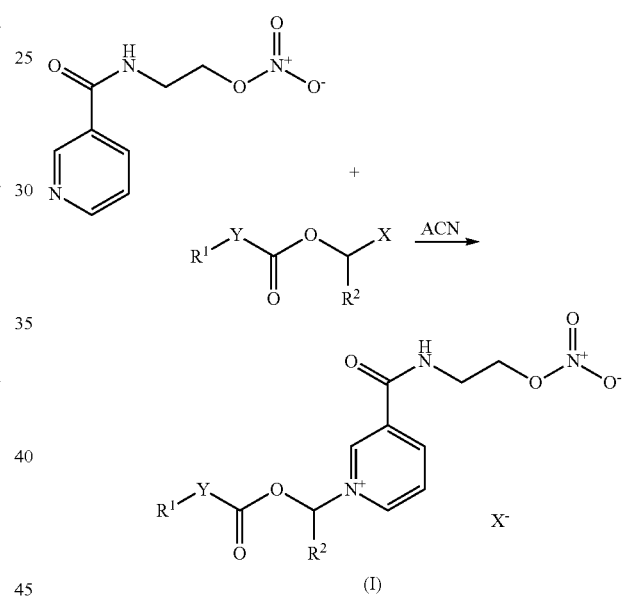

wherein X, Y, R$^1$, and R$^2$ are as described herein.

EXAMPLES

Example 1

Preparation of 1-(((3,3-dimethylbutanoyl)oxy)methyl)-3-((2-(nitrooxy)ethyl)carbamoyl)pyridin-1-ium iodide (Compound 1)

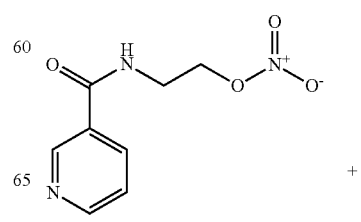

57

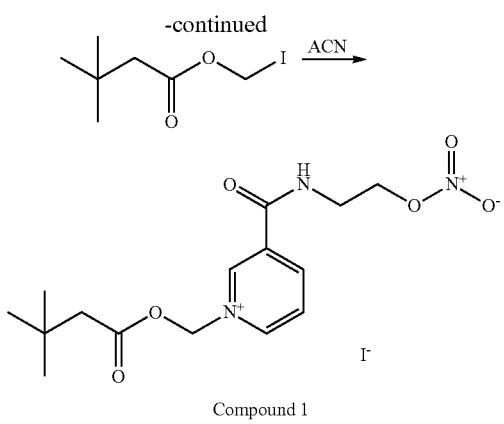

Compound 1

To a solution of nicorandil, (2-(nicotinamido)-ethylnitrate) (0.23 mmol) in acetonitrile (3 mL) was added iodomethyl isopropyl carbamate (0.28 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 1 as a yellow sticky solid.

m/z 340.1 (M$^+$).

Example 2

Preparation of 3-((2-(nitrooxy)ethyl)carbamoyl)-1-(((piperidine-1-carbonyl)oxy)methyl)pyridin-1-ium iodide (Compound 2) (Dugar et al. U.S. Pat. No. 9,359,376)

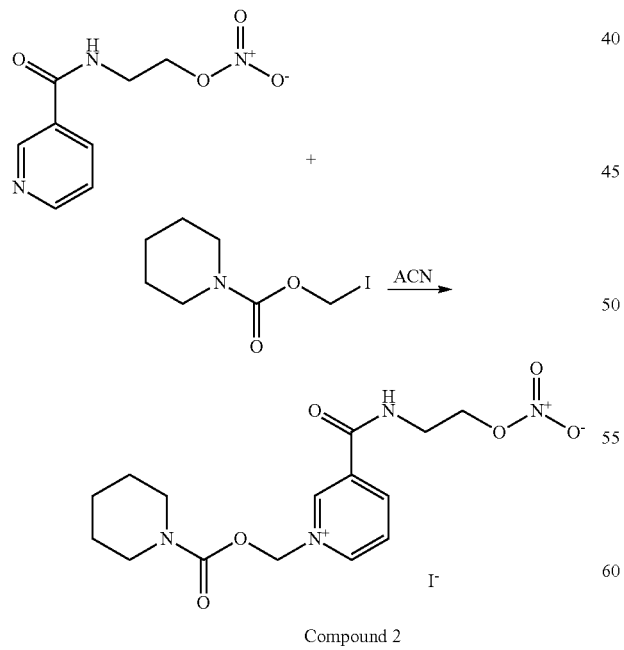

Compound 2

To a solution of nicorandil, (2-(nicotinamido)-ethylnitrate) (0.56 mmol) in acetonitrile (5 mL) was added iodomethyl 1-piperidinyl carbamate (0.68 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 2 as a yellow solid (0.230 g, 84%). (mp 117-120° C.)

m/z 353.2 (M$^+$)

Example 3

Preparation of 1-((((diisopropylcarbamoyl)oxy)methyl)-3-((2-(nitrooxy)ethyl)carbamoyl)pyridin-1-ium iodide (Compound 3)

Compound 3

To a solution of nicorandil, (2-(nicotinamido)-ethylnitrate) (0.71 mmol) in acetonitrile (5 ml) was added iodomethyl diisopropylcarbamate (0.71 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 3 as a yellow solid (0.220 g, 85%). (mp 122-125° C.).

m/z 369.2 (M$^+$)

Example 4

Preparation of 1-(((tert-butoxycarbonyl)oxy)methyl)-3-((2-(nitrooxy)ethyl)carbamoyl)pyridin-1-ium iodide (Compound 4)

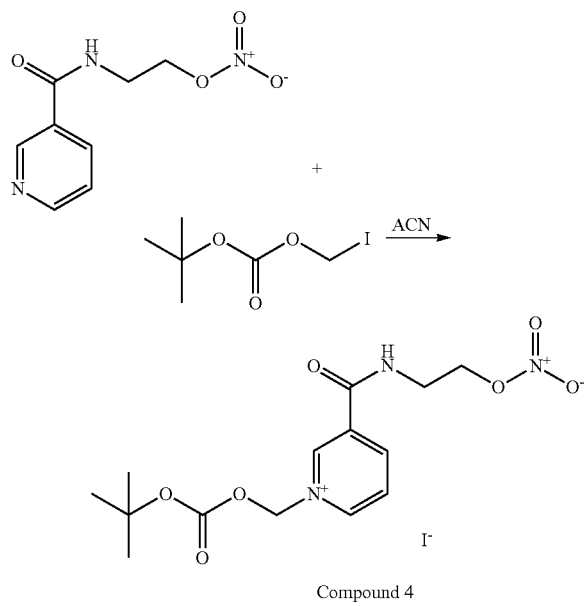

Compound 4

To a solution of nicorandil, (2-(nicotinamido)-ethylnitrate) (0.47 mmol) in acetonitrile (mL) was added tert-butyl (iodomethyl) carbonate (0.52 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 4 as a yellow sticky solid (0.120 g, 54%).

m/z 342.1 ($M^+$)

Example 5

Preparation of 1-(((isopropoxycarbonyl)oxy)methyl)-3-((2-(nitrooxy)ethyl)carbamoyl)pyridin-1-ium iodide (Compound 5)

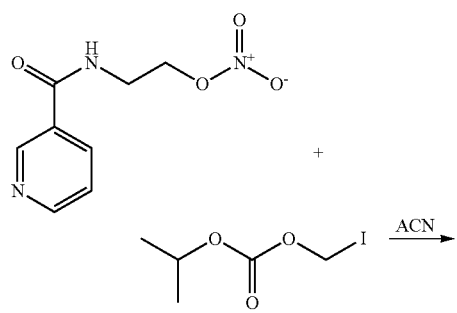

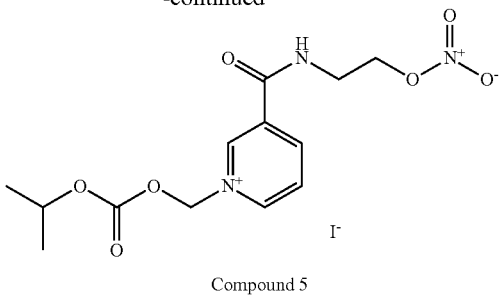

Compound 5

To a solution of nicorandil, (2-(nicotinamido)-ethylnitrate) (0.47 mmol) in acetonitrile (5 ml) was added iodomethyl isopropyl carbonate (0.56 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 5 as a brown sticky material (0.130 g, 60%).

m/z 328.1 ($M^+$)

Example 6

Preparation of (R)-1-(((sec-butoxycarbonyl)oxy)methyl)-3-((2-(nitrooxy)ethyl)carbamoyl)pyridin-1-ium iodide (Compound 6) (Dugar et al. U.S. Pat. No. 9,359,376)

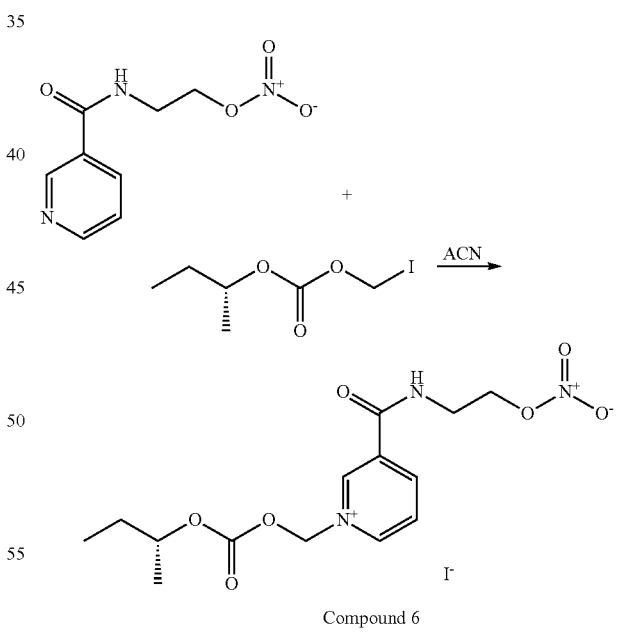

Compound 6

To a solution of nicorandil, (2-(nicotinamido)-ethylnitrate) (0.28 mmol) in acetonitrile (3 ml) was added (R)-sec-butyl (iodomethyl) carbonate (0.28 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 6 as a yellow semisolid.

m/z 342.5 (M$^+$).

Example 7

Preparation of (S)-1-(((sec-butoxycarbonyl)oxy)methyl)-3-((2-(nitrooxy)ethyl)carbamoyl)pyridin-1-ium iodide (Compound 7) (Dugar et al. U.S. Pat. No. 9,359,376)

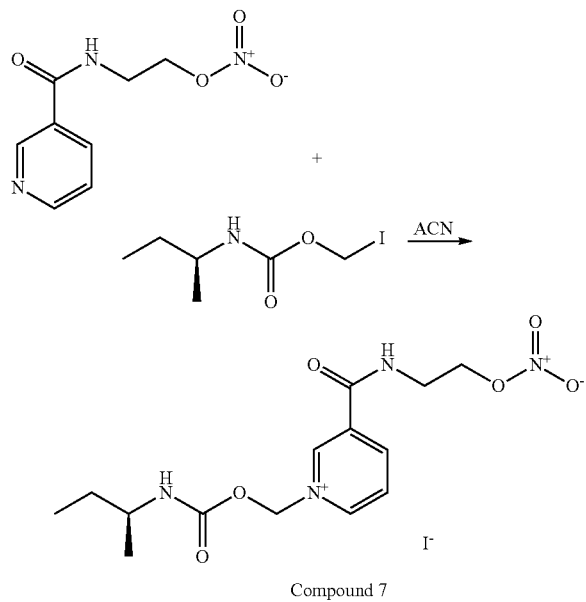

Compound 7

To a solution of nicorandil, (2-(nicotinamido)-ethylnitrate) (0.28 mmol) in acetonitrile (3 mL) was added iodomethyl (S)-sec-butyl (iodomethyl) carbonate (0.28 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 7 as a yellow semisolid.

m/z 342.5 (M$^+$).

Example 8

Preparation of (S)-1-(((1-cyclohexylethylcarbamoyl)oxy)methyl)-3-((2-(nitroxy)ethyl)carbamoyl)pyridine-1-ium iodide (Compound 8) (Compound A) (Dugar et al. U.S. Pat. No. 9,359,376)

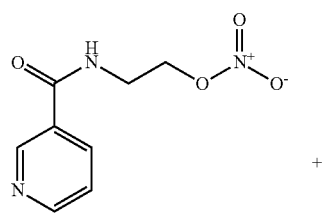

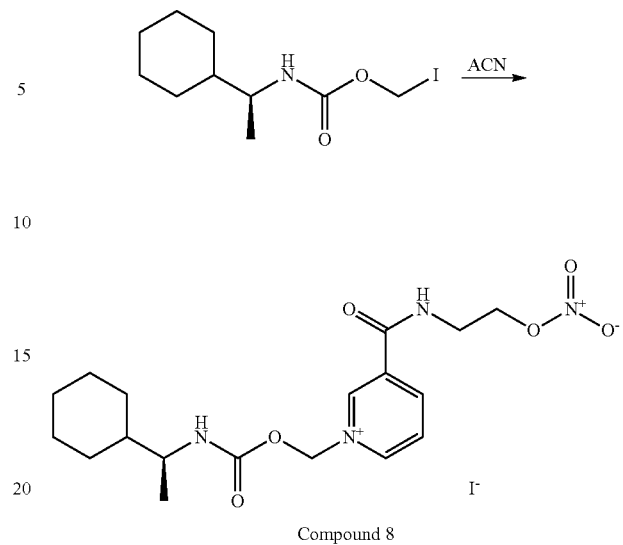

Compound 8

To a solution of nicorandil, (2-(nicotinamido)-ethylnitrate) (0.28 mmol) in acetonitrile (3 mL) was added iodomethyl (S)-(1-cyclohexylethyl) carbamate (0.28 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 8 as a yellow solid (mp 94-98° C.).

m/z 395.5 (M$^+$).

$^1$H NMR (300 MHz, DMSO-d$_6$): δ 9.53 (s, 1H), 9.45 (s, 1H), 9.28 (d, J=6.3 Hz, 1H), 9.03 (d, J=8.1 Hz, 1H), 8.36 (dd, J=8.1, 6.3 Hz, 1H), 7.81 (d, J=9 6.3 Hz, 1H), 6.43 (dd, J=15.5, 6.6 Hz, 2H), 4.69 (t, J=5.1 Hz, 2H), 3.71 (dd, J=10.5, 5.1 Hz, 2H), 3.41 (m, 1H), 1.61 (m, 5H), 0.79-1.25 (m, 9H).

Example 9

Preparation of (R)-1-(((1-cyclohexylethylcarbamoyl)oxy)methyl)-3-((2-(nitroxy)ethyl)carbamoyl)pyridine-1-ium iodide (Compound 9) (Dugar et al. U.S. Pat. No. 9,359,376)

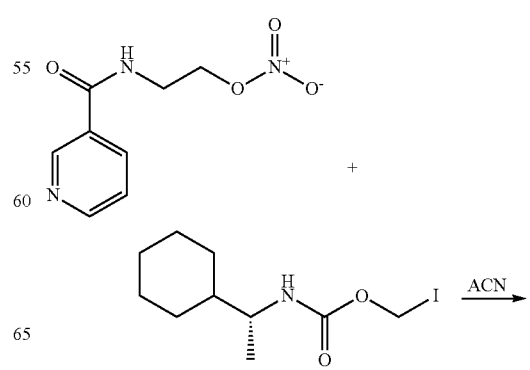

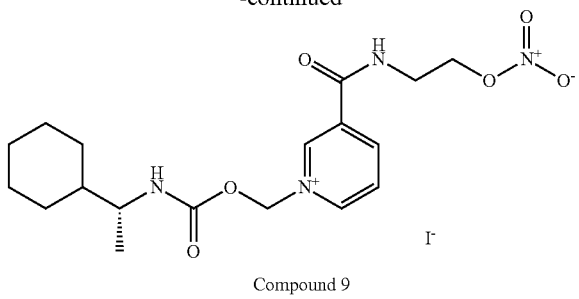

Compound 9

To a solution of nicorandil, (2-(nicotinamido)-ethylnitrate) (0.28 mmol) in acetonitrile (3 mL) was added iodomethyl (R)-(1-cyclohexylethyl) carbamate (0.28 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 9 as a yellow solid. (mp 98-102° C.)

m/z 395.5 (M$^+$).

Example 10

Preparation of 1 1-((isobutyryloxy)methyl)-3-((2-(nitrooxy)ethyl)carbamoyl)pyridin-1-ium iodide (Compound 10)

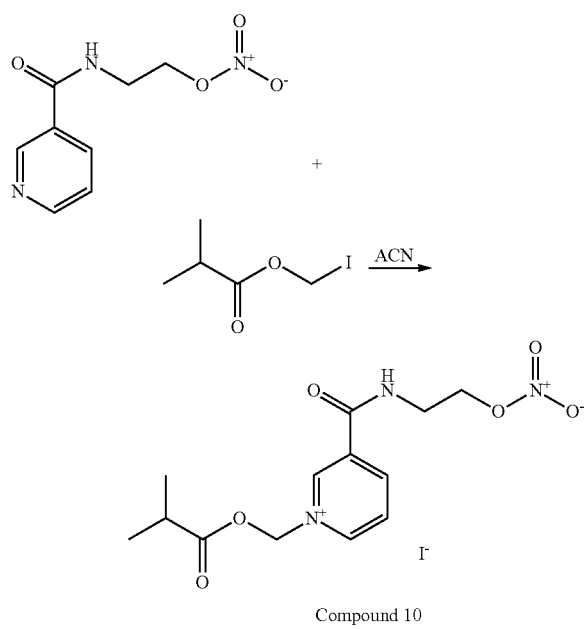

Compound 10

To a solution of nicorandil, (2-(nicotinamido)-ethylnitrate) (0.47 mmol) in acetonitrile (5 mL) was added iodomethyl isobutyrate (0.71 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 10 as a brown sticky material.

m/z 312.1 (M$^+$)

Example 11

Preparation of 1-(1-(((diisopropylcarbamoyl)oxy)ethyl)-3-((2-(nitrooxy)ethyl)carbamoyl)pyridin-1-ium iodide (Compound 11)

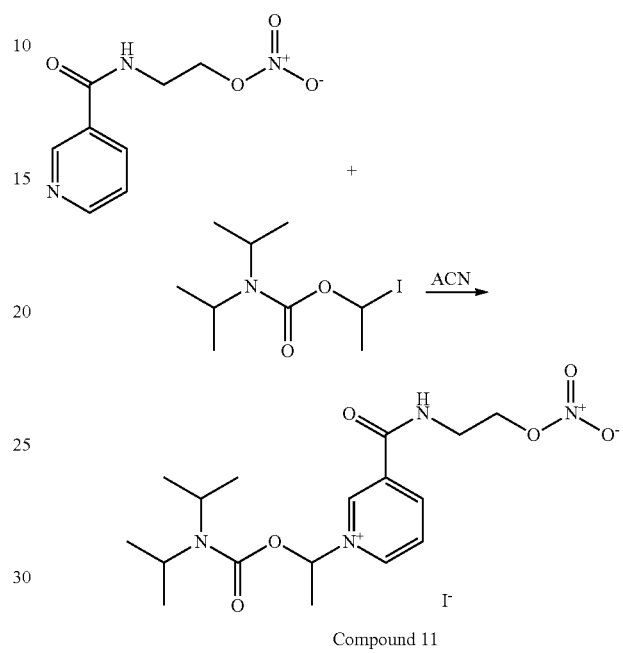

Compound 11

To a solution of nicorandil, (2-(nicotinamido)-ethylnitrate) (0.23 mmol) in acetonitrile (3 ml) was added 1-iodoethyl diisopropylcarbamate (0.23 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 11 as a yellow sticky material (0.042 g, 35%).

m/z 383.4 (M$^+$).

Example 12

Preparation of 1-(((ethoxycarbonyl)oxy)methyl)-3-((2-(nitrooxy)ethyl)carbamoyl)pyridin-1-ium iodide (Compound 12)

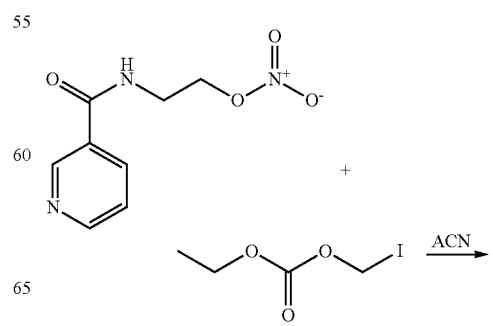

-continued

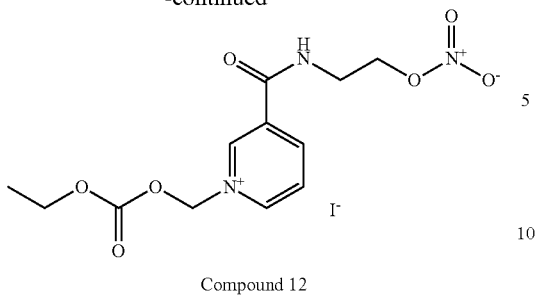

Compound 12

To a solution of nicorandil, (2-(nicotinamido)-ethylnitrate) (0.47 mmol) in acetonitrile (5 mL) was added ethyl (iodomethyl) carbonate (0.71 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 12 as a brown sticky material (0.150 g, 77%).

m/z 314.1 (M$^+$)

Example 13

Preparation of 1-(((isopropylcarbamoyl)oxy)methyl)-3-((2-(nitroxy)ethyl)carbamoyl)pyridine-1-ium iodide (Compound 13) (Dugar et al. U.S. Pat. No. 9,359,376)

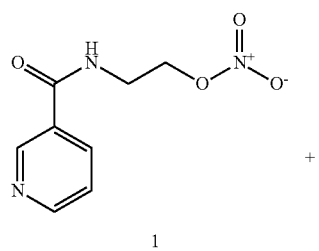

-continued

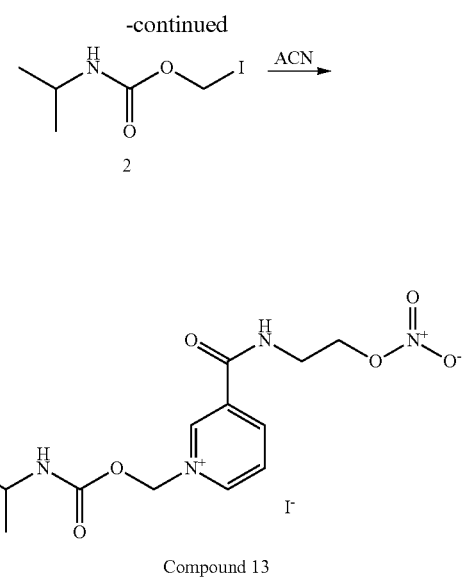

Compound 13

To a solution of nicorandil, (2-(nicotinamido)-ethylnitrate) (0.28 mmol) in acetonitrile (3 mL) was added iodomethyl isopropyl carbamate (0.28 mmol) dropwise. The resulting mixture was stirred overnight at RT. The progress of the reaction was monitored by TLC. The excess of acetonitrile was removed under vacuum and the resulting residue was dissolved in MeOH and washed with an excess of diethyl ether. This process was repeated twice and the solvent was evaporated under vacuum to get titled compound 13 as a yellow sticky solid (0.085 g, 88%).

m/z 327 (M$^+$).

$^1$H NMR (DMSO-d6, 300 MHz): δ ppm 9.54 (s, 1H), 9.43-9.46 (m, 1H), 9.27-9.29 (d, 1H), 9.01-9.04 (d, 1H), 8.33-8.38 (m, 1H), 7.86-7.88 (m, 1H), 6.41 (s, 2H), 4.67-4.70 (t, 2H), 3.69-3.74 (m, 2H), 3.52-3.63 (m, 1H), 1.04-1.11 (m, 6H).

TABLE 1

Representative Compounds of the Invention

| Compound # | Structure | Salt |
|---|---|---|
| Nicorandil | 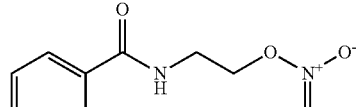 $C_8H_9N_3O_4$ | N/A |
| 1 |  $C_{15}H_{22}N_3O_6^+$ | Iodide |

TABLE 1-continued

Representative Compounds of the Invention

| Compound # | Structure | Salt |
| --- | --- | --- |
| 2 | $C_{15}H_{21}N_4O_6^+$ | Iodide |
| 3 | $C_{16}H_{25}N_4O_6^+$ | Iodide |
| 4 | $C_{14}H_{20}N_3O_7^+$ | Iodide |
| 5 | $C_{13}H_{18}N_3O_7^+$ | Iodide |
| 6 | $C_{14}H_{20}N_3O_7^+$ | Iodide |

TABLE 1-continued
Representative Compounds of the Invention
| Compound # | Structure | Salt |
|---|---|---|
| 7 | 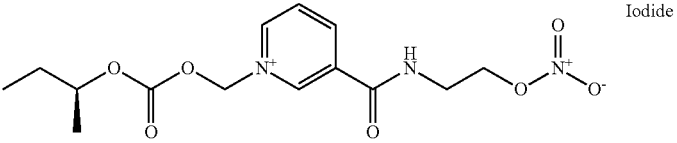 $C_{14}H_{20}N_3O_7^+$ | Iodide |
| 8 | 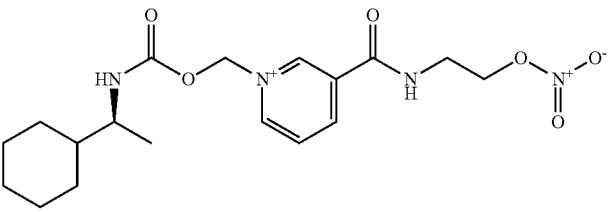 [SMILES: C[C@H](NC(=O)OC[n+]1cccc(C(=O)NCCO[N+](=O)[O-])c1)C1CCCCC1] $C_{18}H_{27}N_4O_6^+$ | Iodide |
| 9 | 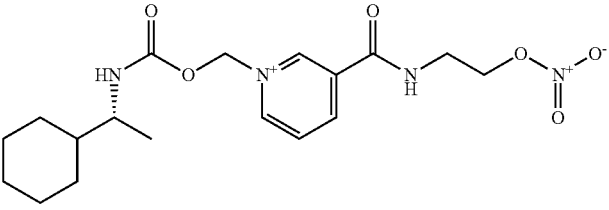 [SMILES: C[C@@H](NC(=O)OC[n+]1cccc(C(=O)NCCO[N+](=O)[O-])c1)C1CCCCC1] $C_{18}H_{27}N_4O_6^+$ | Iodide |
| 10 | 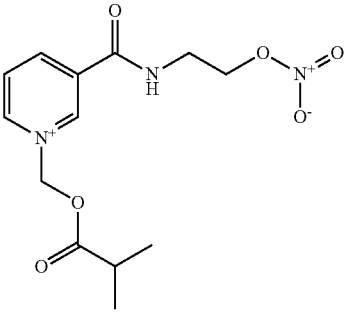 [SMILES: CC(C)C(=O)OC[n+]1cccc(C(=O)NCCO[N+](=O)[O-])c1] $C_{13}H_{18}N_3O_6^+$ | Iodide |
| 11 | 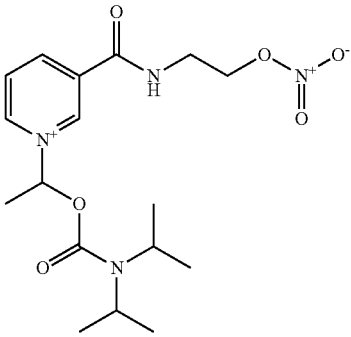 [SMILES: CC(C)N(C(=O)OC(C)[n+]1cccc(C(=O)NCCO[N+](=O)[O-])c1)C(C)C] $C_{17}H_{27}N_4O_6^+$ | Iodide |

TABLE 1-continued

Representative Compounds of the Invention

| Compound # | Structure | Salt |
|---|---|---|
| 12 | $C_{12}H_{16}N_3O_7^+$ | Iodide |
| 13 | $C_{13}H_{19}N_4O_6^+$ | Iodide |

Additional Exemplary Compounds of the Invention

Other compounds of the invention have been or can be prepared according to the synthetic methods, or some variations thereof, described herein. The compounds can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The following additional compounds are or can be prepared from readily available starting materials using the following general methods and procedures:

$C_{18}H_{27}N_4O_6^+$   I⁻

Pharmacokinetics Testing

Example 101 (PK)

Pharmacokinetics (PK) Protocol: Rat

Pharmacokinetics study was carried out to evaluate the plasma exposure of Compound A in rat. The dosing vehicle used in this study was PEG400. 1, 3, 10 mg/kg oral dosing was done in overnight fasted SD rats and the parent drug generated was monitored. Also presence of modified drug was checked. After oral (PO) dosing blood was collected by serial bleeding at 8 different time points in heparinised tubes. Blood samples were centrifuged at 10,000 rpm for 5 min. at 4° C. to obtain the plasma, which were aspirated into separate labeled tubes and stored at −80° C. Extraction solvent was added to plasma, was vortexed and shaken on shaker for 10 minutes, centrifuged at 10,000 rpm for 10 minutes at 4° C. Supernatant was kept for analysis. Acetonitrile and plasma calibration curves were generated and percentage of drug recovery from plasma determined. Quantitative analysis was done by liquid chromatography tandem mass spectrometer (API3000 LC-MS/MS). Cmax, Tmax, AUC and t½ were calculated using Graph Pad PRISM version 5.04 and the results are depicted in Table 2.

TABLE 2

Pharmacokinetics parameters for Compound
A (1, 3, 10 mg/kg oral dose in SD rats)

| Parameters Rat PK | Compound A (1 mpk oral) | Compound A (3 mpk oral) | Compound A (10 mpk oral) | Nicorandil (3 mpk oral) |
|---|---|---|---|---|
| Cmax (nM) | 2529.42 | 9083.49 | 34705.8 | 7767.31 |
| Tmax (hr) | 2.00 | 1.17 | 2.0 | 1.17 |
| AUC (nM-hr) | 9788 | 46437.67 | 127639.0 | 20347.50 |
| Elimination $t_{1/2}$ (hr) | 2.28 | 3.67 | 2.1 | 3.43 |

Example 102 (PK)

Pharmacokinetics (PK) Protocol: Dog

Pharmacokinetics study was carried out to evaluate the plasma exposure of Compound A in dog. Male Beagle dogs which were fasted overnight were dosed 3 mg/kg Compound A by oral route. 0.5 ml blood was collected at each time point from the femoral vein via direct stick at defined time points. in tubes containing anticoagulant. Blood samples were centrifuged at 10,000 rpm for 5 min. at 4° C. to obtain the plasma, which were aspirated into separate labeled tubes and stored at −80° C. Extraction solvent was added to plasma, was vortexed and shaken on shaker for 10 minutes, centrifuged at 10,000 rpm for 10 minutes at 4° C. Supernatant was kept for analysis. Acetonitrile and plasma calibration curves were generated and percentage of drug recovery from plasma determined. Quantitative analysis was done by liquid chromatography tandem mass spectrometer (API3000 LC-MS/MS). Cmax, Tmax, AUC and t½ were calculated using Graph Pad PRISM version 5.04 and the results are depicted in Table 3.

TABLE 3

Pharmacokinetics parameters for Compound
A (3 mg/kg oral dose in Beagle dog)

| Parameters Dog PK | Compound A (3 mpk oral) | (Nicorandil) (3 mpk oral) |
|---|---|---|
| Cmax (nM) | 9284 | 2113 |
| Tmax (hr) | 0.7 | 0.3 |
| AUC (nM-hr) | 17714 | 3685 |
| Elimination $t_{1/2}$ (hr) | 2.5 | 3.2 |

Compound A showed excellent plasma exposure in rat and dog. In both the cases only parent drug was detected in plasma and no modified drug was detected. Plasma exposure in rat displayed dose linearity. In dog, plasma exposure was significantly higher as shown by higher AUC and Cmax Pharmacokinetics parameters for Compound A (3 mg/kg oral dose in Beagle dog) (Table 4).

TABLE 4

Rat Pharmacokinetic Data (3 mpk (eq.), PO)
Measuring plasma levels of Nicorandil.

| Compd # | $T_{max}$ (min) | $T_{1/2}$ (hr) | $C_{max}$ (µM) | AUC (µM) |
|---|---|---|---|---|
| 1 | 10 | 1.25 | 14.2 | 20.6 |
| 2 | 10 | 1.63 | 45.4 | 57.1 |
| 3 | 30 | 2.4 | 16.4 | 32.2 |
| 4 | 30 | 2.42 | 6.2 | 12.5 |
| 5 | 33 | 1.98 | 2.6 | 4.5 |
| 6 | 36 | 2.52 | 12.4 | 23.7 |
| 7 | 40 | 2.56 | 5 | 10 |

TABLE 4-continued

Rat Pharmacokinetic Data (3 mpk (eq.), PO)
Measuring plasma levels of Nicorandil.

| Compd # | $T_{max}$ (min) | $T_{1/2}$ (hr) | $C_{max}$ (µM) | AUC (µM) |
|---|---|---|---|---|
| 8 | 70 | 3.67 | 9.1 | 46.4 |
| 9 | 70 | 2.54 | 11.7 | 33.2 |
| Nicorandil | 70 | 3.43 | 7.8 | 20.4 |
| 10 | 80 | 3.3 | 5.8 | 15 |
| 11 | 80 | 2.07 | 5.1 | 16.1 |
| 12 | 102 | 4.82 | 3.5 | 11.1 |
| 13 | 110 | 4.85 | 6.6 | 28.5 |

Example 201 (Pharm Assays)

Efficacy Studies of Compound A in Diabetic Nephropathy Animal Studies Using eNOSKO Mice All animal experiments will be performed in accordance the INSTITUTIONAL ANIMAL CARE AND USE COMMITTEE (IACUC) protocols. Male C57BL/6J-Nos3tm1nc mice (eNOSKO mice) will be purchased from Jackson Laboratory (Bar Harbor, ME) at 8 wk of age. Mice will be fed a standard laboratory chow ad libitum. Diabetic nephropathy will be induced by intraperitoneal injections of streptozotocin (50 mg/kg/day for 5 consecutive days) dissolved in 10 mM citrate buffer, pH 4.5. Diabetes is defined as nonfasting blood glucose 250 mg/dl using a blood glucose meter (One Touch Ultra; Life Scan, Milpitas, CA). Only mice that developed hyperglycemia at 4 wk will be included in the study. Mice will be divided into four subgroups: 1) a nondiabetic group, 2) a Compound A-treated nondiabetic group, 3) a diabetic group, and 4) a Compound A-treated diabetic group (n 8/group) (Tanabe et al., Am. J. Physiol Renal Physiol 2012, 302, 151-160). At 4 wk when the onset of diabetes is confirmed in all animals, 30 mg/kg of Compound A (Chugai Pharmaceutical, Tokyo, Japan) will be started. To constantly administer the same amount of Compound A (30 mg/kg/day), the concentration of Compound A in the drinking water will be adjusted every 4 days along with as per the water intake volume. Water bottles will be monitored daily throughout the study to ensure no leakage occurred. Systolic blood pressure will be measured every other week using a tail-cuff sphygmomanometer (Visitech BP-2000; Visitech Systems, Apex, NC). Urine will be collected overnight using metabolic cages (Techniplast, Exton, PA). All the mice will be euthanized 8 wk after starting Compound A treatment to obtain blood samples and kidney tissues.

Laboratory Studies

Urine albumin, urine 8-hydroxy-2-deoxyguanosine (8-OHdG), and urine creatinine will be measured with Albuwell M (Exocell, Philadelphia, PA), an OxiSelect Oxidative DNA Damage ELISA Kit (Cell Biolabs, San Diego, CA), and Creatinine LiquiColor Test (Enzymatic Methodology; Stanbio, Boerne, TX), respectively. Serum creatinine concentration will be analyzed with HPLC-tandem mass spectrometry (MS/MS; Applied Biosystems 3200 Qtrap). Creatinine and [2H3] creatinine (CDN isotopes) will be detected in the multiple reaction monitoring mode, monitoring the transitions of the m/z from 114 to 44.2 and m/z from 117 to 47.2, respectively. Serum levels of P-selectin and ICAM-1 will be measured with a Mouse P-selectin/CD62 Quantikine ELISA kit and Mouse ICAM-1/CD54 Quantikine ELISA kit, respectively (R&D Systems, Minneapolis, MN).

Histological Analysis

Formalin-fixed, paraffin-embedded sections (2.5-m) will be stained with the periodic acid-Schiff reagent (PAS) for light microscopy. On coronal sections of the kidney, all glomeruli (50-100 glomeruli) will be examined for evaluation of mesangiolysis and glomerulosclerosis. Glomerulosclerosis will be defined as obstruction of the capillary lumen caused by mesangial expansion or collapsed capillaries, whereas the degree of mesangiolysis will be calculated as the number of glomeruli with mesangiolysis (dissolution of the mesangial matrix) divided by that of total glomeruli. Kidney sections will be observed by two investigators in a blinded manner.

Immunohistochemistry

Either formalin or methyl Carnoy's solution-fixed, paraffin-embedded sections will be used for immunohistochemistry. The following antibodies will be used as primary antibodies: 1) rabbit anti-type IV collagen antibody (Chemicon International, Temecula, CA); 2) rat anti-mouse F4/80 antibody (Serotec, Raleigh, NC); 3) rabbit anti-WT-1 antibody (Santa Cruz Biotechnology, Santa Cruz, CA); 4) goat anti-8-OHdG antibody (Abcam, Cambridge, MA); 5) rabbit anti-nitrotyrosine antibody (Chemicon); and 6) rabbit anti-NPHS2 (podocin) antibody (Abcam). Briefly, after deparaffinization, the sections will be treated with 3% H2O2 for 10 min to inactivate endogenous peroxidase activity. For F4/80, 8-OHdG, and nitrotyrosine, the sections will be treated with 10 mM citrate buffer (pH 6.0) for 30 min in a steamer for antigen retrieval. After incubation with a background sniper (Biocare Medical, Concord, CA) for 15 min, sections will be incubated with primary antibodies overnight at 4° C. The sections will be also incubated with rabbit anti-IgG secondary antibodies for 30 min before immunoperoxidase staining will be conducted using the Mach2 rabbit HRP polymer (Biocare Medical). Slides will be counterstained with methyl green. The number of positive cells for F4/80 will be counted in all glomeruli at 400 magnification in each section. After immunohistochemistry for WT-1 will be performed, podocyte number per glomerulus will be calculated using the Weibel-Gomez method. Ten representative glomeruli will be analyzed on each section for this calculation. To assess the type IV collagen- and podocin-positive area, the digital images at 400 magnification will be analyzed using Image scope software (Aperio Technologies, Vista, CA). The percent positive area will be determined as the 3,3-diaminobenzidine-positive pixel values per examined interest area from all glomeruli in each section. Immunofluorescence in the Mouse Kidney Double immunofluorescence staining will be performed. Briefly, frozen sections (4-m) will be fixed in acetone for 10 min. The sections will be blocked with 5% animal serum complex and then incubated overnight with primary antibodies, rabbit anti-ABCC9 (sulfonylurea receptor 2; SUR-2) antibody (Abcam), rabbit anti-cGMP antibody (Chemicon), or mouse monoclonal anti-synaptopodin antibody (Novus Biologicals, Littleton, CO), at 4° C. After incubation with either Alexa Fluor 488-labeled goat anti-rabbit IgG (Invitrogen, Carlsbad, CA) or Alexa Fluor 546-labeled goat antimouse IgG (Invitrogen) for 2 h at room temperature, sections will be mounted with vectashield anti-fade mounting medium (Vector Labs, Burlingame, CA). A laser-scanning confocal microscope LSM 510 META (Carl Zeiss Microimaging, Thornwood, NY) will be used to obtain images.

Western Blotting

Kidney tissues will be homogenized in cell lysis buffer (Cell Signaling, vDanvers, Mass.) at 4° C. Briefly, samples will be processed for SDS-PAGE and electrotransferred onto a nitrocellulose membranes. A rabbit anti-nitrotyrosine (Chemicon) antibody, rabbit anti-actin antibodies (Sigma-Aldrich, St. Louis, MO), an HRP-labeled antirabbit IgG antibody (Cell Signaling), and Immun Star HRP (Bio-Rad, Hercules, CA) will be used. The density of each band will be determined using National Institutes of Health Image software and expressed as a value relative to the density of the corresponding band of actin.

Cell Culture

Conditionally immortalized human podocytes will be cultured in RPMI 1640 medium (Mediatech, Manassas, VA) supplemented with 10% FBS, penicillin (100 U/l), streptomycin (100 g/l), and Insulin-Transferrin-Selenium A supplements (Invitrogen). Cells will be cultured at 33° C. to enhance the expression of large T antigen and propagate podocytes, followed by incubation for 10 days at 37° C. to induce differentiation into mature podocytes before initiation of experiments. For the experimental studies, podocytes will be cultured in DMEM with 5.5 mM normal glucose (NG), NG19.5 mM mannitol (NGMan), 25 mM high glucose (HG), and HG105 M Compound A (HGNico) for 72 h.

PCR

Total RNA will be extracted from cultured podocytes using an RNeasy Mini Kit (Qiagen, Chatsworth, CA). The first-strand cDNA will be synthesized from 1 g of total RNA using an iScript cDNA Synthesis Kit (Bio-Rad). For the detection of SUR2A and SUR2B mRNA, the following oligonucleotide primers will be used: SUR2A, (SEQ ID NO: 1) 5=-TGAGGGTATTTTAGTGGAGTGTG-3=(forward) and (SEQ ID NO: 2) 5=-CAAAGTGGAAAAGAGGC-CATTC-3=(reverse); SUR2B, (SEQ ID NO: 3) 5=-TGGTGACAATAGCTCATCGAG-3=(forward) and (SEQ ID NO: 4) 5=-TCCATTTTCCTGAGCCAAGAG-3= (reverse); and -actin, (SEQ ID NO: 5) 5=-TGAGATGCGTTGTTACAGGAAG-3=(forward) and (SEQ ID NO: 6) 5=-GTGGACTTGGGAGAGGACTG-3= (reverse). The PCR program will be optimized and performed as denaturation at 95° C. for 3 min followed by 50 cycles of amplification (SUR2A and SUR2B, 95° C. for 30 s, 54° C. for 30 s, 72° C. for 1 min; -actin, 95° C. for 30 s, 56° C. for 30 s, 72° C. for 1 min, respectively) using the MyiQ Single-Color Real-Time PCR Detection System (Bio-Rad). The amount of PCR products will be normalized with -actin mRNA to determine the relative expression ratio for SUR2A and SUR2B mRNA.

ROS Detection Assay in Cultured Podocytes

An Image-iT LIVE Green Reactive Oxygen Species Detection Kit (Invitrogen) will be used to measure the generation of ROS. Briefly, podocytes will be incubated in PBS containing 25 M 5-(and 6)-carboxy-2=,7=-dichlorodihydrofluorescein diacetate (carboxy-H2DCFDA) for 30 min at 37° C. in the dark. This probe is converted by intracellular esterase and ROS to carboxy-DCF, which emits a bright green fluorescence. After incubation, the cells will be washed with PBS three times and observed by a laser-scanning confocal microscope LSM 510 META (Carl Zeiss) to obtain images. The intensity in podocytes will be measured by Zen 2009 software (Carl Zeiss). A total of 10 fields (at 400) will be examined to determine the averaged value of cells in each image.

Cell Number

A conventional MTT assay will be used to assess cultured podocyte number. Podocytes will be seeded in 96-well plates at 10,000 cells/well and allowed to differentiate at 37° C. for 10 days. Seventy two hours after stimulation by NG or HG medium with or without Compound A, 20 l of thiazolyl blue tetrazolium bromide (Sigma-Aldrich) dissolved in PBS at 5 mg/ml will be added into each well containing 100 l of medium, and the plate will be incubated for 3 h at 37° C. MTT solvent (4 mM HCl and 0.10% P-40 in isopropanol) will be used before absorbance will be read at 590 nm with a reference filter of 620 nm. Data will be expressed as values relative to NG.

Statistical Analysis

All values are expressed as means SD. Statistical analysis will be performed with ANOVA using Tukey's (for in vivo experiments) or Bonferroni's (in vitro experiments) method to compare four groups. A level of $P<0.05$ will be considered statistically significant.

Example 202 (Pharm Assays)

Efficacy Studies of Compound a in Chronic Kidney Disease

Animal Studies Using Remnant Kidney (RK) Model to Study CKD

All animal experiments will be performed in accordance with, and approved by, the Institute Animal Care and Use Committee of the institution. Male Sprague-Dawley rats (200-240 g) will undergo baseline blood pressure (BP) and renal function assessments and will be randomly assigned to the RK group or the sham-operated control group. For the RK group, a right subcapsular nephrectomy will be performed and followed by surgical resection of the upper and lower one-thirds of the left kidney (Tamura et al., Am. J. Physiol Renal Physiol 2012, 303, 339-349). Rats will be divided into four subgroups: 1) sham group, 2) RK group, 3) RK with low dose Compound A (3 mg/kg/day), and 4) RK with high dose Compound A (30 mg/kg/day) (n 7 for each group). All rats will be fed ad libitum. Two weeks after surgery, rats will be randomized based on blood urea nitrogen (BUN) level before starting Compound A treatment (Chugai Pharmaceutical, Tokyo, Japan). To constantly administer the same amount of Compound A (30 mg/kg/day), the concentration of Compound A in the drinking water will be adjusted every 4 days, along with the water intake volume. Water bottles will be monitored daily throughout the study to ensure that no leakage occurred. Systolic BP will be measured at 0, 4, and 12 wk using a tail-cuff sphygmomanometer (Visitech BP-2000; Visitech Systems, Apex, NC). Urine will be collected overnight using metabolic cages (Techniplast, Exton, PA) before death. All of the rats will be killed at 12 wk to obtain blood samples and kidney tissues.

Laboratory Studies

Urine albumin, urine 8-hydroxy-2=-deoxyguanosine (8-OHdG), xanthine oxidase activity, and urine creatinine will be measured with Nephrat (Exocell, Philadelphia, PA), OxiSelect Oxidative DNA Damage ELISA Kit (Cell Biolaboratories, San Diego, CA), xanthine oxidase assay kit (Cayman, Ann Arbor, MI), and Creatinine LiquiColor Test (enzymatic methodology; Stanbio, Boerne, TX), respectively. Uric acid concentration in the renal cortex will be determined with the Quantichrom uric acid assay kit (Bioassay System, Hayward, CA). In contrast, serum levels of uric acid, BUN, and creatinine will be determined by VetACE Clinical Chemistry System (Alfa Will besermann, NJ). Serum cystatin-C concentration will be determined by Mouse/Rat Cystatin-C ELISA kit (R&D Systems, Minneapolis, MN). To examine the renal NO, the concentration of urinary nitrate (NO3) and nitrite (NO2) will be determined by NO analyzer 280i (SIEVERS, Boulder, CO).

Histological Analysis

Formalin-fixed, paraffin-embedded sections (2.5 m) will be stained with the periodic acid-Schiff reagent for light microscopy. On coronal sections of the kidney, all glomeruli (50-100 glomeruli) will be examined to evaluate glomerulosclerosis. Glomerulosclerosis will be defined as obstruction of capillary lumen caused by mesangial expansion or collapsed capillaries. Kidney sections will be observed by two investigators in a blinded manner. Primary antibodies for immunohistochemistry and Western blotting. Goat anti-human type IV collagen antibody (Southern Biotech, Birmingham, AL) and mouse anti-rat CD68 antibody (AbD Serotec, Oxford, UK) will be used for glomerular injury. Rabbit antihuman WT-1 antibody (Santa Cruz, Santa Cruz, CA) and rabbit anti-human NPHS2 (podocin) antibody (Abcam, Cambridge, MA) will be used to detect podocytes. To examine the tubulointerstitial injury, goat anti-human type III collagen antibody (Southern Biotech) will be used. Mouse anti-rat CD11b/c equivalent antibody (OX42) (Abcam) will be for identifying the phenotype of immune cell in the interstitium. Goat anti-human sulfonylurea receptor (SUR)-2B (C-15) antibody (Santa Cruz) and rabbit anti-human ABCC9 antibody (Abcam) will be for detecting of SUR. Rabbit anti-rat manganese SOD (MnSOD) (Enzo Life Sciences, Farmingdale, NY), rabbit anti-human xanthine oxidase (H-110) antibody (Santa Cruz), mouse anti-nitrotyrosine antibody (Millipore, Billerica, MA), mouse anti-GAPDH antibody (Millipore), and rabbit anti-mouse heme oxygenase-1 antibody (Stressgen, Ann Arbor, MI) will be also used.

Immunohistochemistry

Either formalin or methyl Carnoy's solution-fixed, paraffin-embedded sections will be used for immunohistochemistry. To identify the cell type, serial section (1.5 m) technique will be used with specific markers of cell type. Briefly, after deparaffinization, the sections will be treated with 3% $H_2O_2$ for 10 min to inactivate endogenous peroxidase activity. For WT-1, CD68, CD11b/c, and SUR2, the sections will be treated with 10 mM citrate buffer (pH 6.0) for 30 min in a steamer for antigen retrieval. The sections will be incubated with primary antibodies overnight at 4° C., followed by treatment with secondary antibodies for 30 min. Color development will be achieved using diaminobenzidine with/without nickel chloride. All glomeruli at 400 magnification or 15 fields (each field/0.4 mm2) in each section will be used to count the number of positive cells for CD68, CD11b/c, or WT-1. To assess the type IV collagen and podocin positive area, the digital images at 400 magnification will be analyzed using Image scope software (Aperio Technologies, Vista, CA). The percent positive area will be determined as the diaminobenzidine-positive pixel per total pixel in interest area from all glomeruli in each section. Likewise, positive area for type III collagen in interstitium will be also determined as percent positive area with 15 fields (each field/0.4 mm2).

Western Blotting

Kidney cortex will be homogenized in cell lysis buffer (Cell Signaling, Danvers, MA) at 4° C. Briefly, samples will be processed for SDS-PAGE, and electrotransferred onto a nitrocellulose membrane. After overnight incubation with primary antibody at 4° C., membrane will be incubated with secondary antibody linked with horseradish peroxidase for 1 h at RT. Signal will be detected by Immun Star HRP (Bio-Rad, Hercules, CA). The density of each band will be determined using National Institutes of Health Image software and expressed as a value relative to the density of the corresponding band of the -actin or GAPDH.

Cell Culture

RAW264.7 cells (ATCC, Manassas, VA), a macrophage cell line, will be cultured in Dulbecco's modified Eagle's medium (Cellgro, Manassas, VA), supplemented with 10% FBS, penicillin (100 U/l), and streptomycin (100 g/l). Subconfluent cells will be stimulated with angiotensin II (Sigma-Aldrich) at 37° C. after pretreatment of various concentrations of Compound A for 30 min in serum-free medium. Eight hours after glibenclamide (Sigma) exposure, xanthine oxidase expression will be examined. Each experiment will be repeated at least four times.

Statistical Analysis

All values are expressed as means SE.Statistical analysis will be performed with ANOVA using Tukey's method. A level of $P<0.05$ will be considered statistically significant.

Example 203 (Pharm Assays)

Efficacy Studies of Compound a in Acute Kidney Injury

Animal Studies in Drug Induced AKI Model

All animal experiments will be performed in accordance with, and approved by, the Institute Animal Care and Use Committee of the institution. Adult male Wistar rats (150-200 g) will be used for the studies. They will be housed in standard rat cages (421 Å~290 Å~190 mm). All animals will be exposed to 12 h light-dark cycles and allowed access ad libitum to drinking water and rat chow.

Drug Dose that Results in AKI

A rat model of Tenofovir disoproxil fumarate (TDF) nephrotoxicity which was standardized recently in Isaac laboratory will be used (8). TDF at a dose of 600 mg/kg body wt/day orally for 5 weeks (which is 12× clinical dose) results in severe damage to the mitochondria of proximal tubules as seen in humans and thus will be utilized for the purpose of this study.

Experimental Design

The rats will be assigned randomly into two groups and will be treated as follows:

Group I (control): The rats in this group (n=6) received sterile water alone by gavage Group II: The rats (n=6) in this group received 600 mg/kg body weight TDF dissolved in sterile water by gavage for 5 weeks. Control animals will be treated with sterile water on the same schedule as TDF treatment and will be killed at the same time for TDF-treated and control rats.

Measurements

Fluid and Food Intake, Mortality Checks, Clinical Observations, and Body Weights Animals will be checked daily for clinical signs of toxicity, morbidity, or death. Body weights will be measured weekly. All the rats will be sacrificed 24 h after the final dose of TDF/sterile water. Twenty-four hours before sacrifice, the rats will be placed individually in metabolic cages, and urine will be collected for biochemical analysis. On the 36th day, blood samples will be collected from the rats under halothane anesthesia, by cardiac puncture into tubes and allowed to clot at room temperature. Thereafter, serum will be separated by centrifugation at 1200×g for 15 min at 4° C. for clinical chemistry. Both the kidneys will be removed and weighed. One kidney will be cut in cross section; a part will be fixed in 10% buffered formalin for light microscopy, and the remaining part will be fixed in 3% glutaraldehyde for electron microscopy. The other kidney will be stored at −70° C. until used.

Morphological Examination of the Kidney

After fixation of kidney tissues in 10% buffered formalin for 24 h at room temperature, the slices will be embedded in paraffin and then sectioned. Four micrometer-thick paraffin sections will be stained with hematoxylin and eosin (H&E) for light microscope examination using a conventional protocol. A minimum of eight fields for each kidney section will be examined and assigned for severity of changes by an observer blinded to the treatments of the animals. Tubular injury will be graded on a semiquantitative scale. Tubular injury will be defined as tubular epithelial necrosis, cast formation, tubular dilatation, and the loss of the brush border. Tubular injury will be scored by grading the percentage of affected tubules under 10 randomly selected, nonoverlapping fields (magnification, 200×) as follows: 0, 0%; 1, 10%; 2, 11-25%; 3, 26-45%; 4, 46-75%; and 5, 76-100%. To score injured tubules, whole tubule numbers per field will be considered as standard under a magnification of 200×. The grading percentage will be calculated in each field as follows: Injury score (%)=Number of injured tubules/Number of whole tubules×100.

Fine Structure of Kidney Tissues

Electron microscope (EM) Studies: The kidney tissues will be fixed in 3% glutaraldehyde and will behed in buffer, postfixed by 1% osmium tetraoxide and will behed in buffer, and, dehydrated in increasing concentrations of alcohol. The tissues will be will behed with propylene oxide and embedded in epoxy-resin embedding medium. Sections (0.5 µm) will be cut with glass knives and stained with toluidine blue for orientation. Ultrathin (900 A°) sections will be cut with a diamond knife, stained with uranyl acetate and lead citrate and examined by EM, evaluated and photographed. Each EM photomicrograph will be reviewed independently by two investigators. Parameters included the presence of structurally abnormal mitochondria, increased numbers of mitochondrial profiles per field, intramitochondrial lamellar bodies, abnormal cristae density, cristae reduplication, mitochondrial swelling, and intramitochondrial paracrystals. The extent of mitochondrial ultrastructural injury in the proximal tubular cells will be then quantitatively assessed (at a scale of 0-5) based on the cell injury staging system. This staging system enumerates the characteristic progression of ultrastructural changes that occurs within cells in various models of inflammatory injury. The association between the degree of mitochondrial injury and the defined stages of cellular injury will be employed to quantify and standardize the severity of ultrastructural injury to the proximal tubular mitochondria.

Serum Clinical Chemistry

Serum will be separated and used for the estimation of phosphate, potassium, bicarbonate, uric acid, glucose, urea, and creatinine.

Urinalysis

Urine samples will be centrifuged to remove suspended material, and the supernatants will be used for the estimation of bicarbonate, phosphate, potassium, and uric acid. Glucose and protein will be semiquantified by dipstick. Low molecular weight proteins in urine will be detected by sodium dodecyl sulfate polyacrylamide gel electrophoresis (SDS PAGE).

Detection of Low Molecular Weight Proteins in Urine by SDS PAGE

Urine proteins will be measured by Lowry's method and fractionated by SDS-PAGE using 8% resolving gel and 5% stacking gel. Each sample containing 100 µg of urinary protein will be mixed with a protein dissociation buffer in the ratio of 1:1 and kept in a boiling water bath for 5 min. Samples will be briefly centrifuged; they will be then loaded onto wells. Running gel buffer (pH 8.6) will be added to an electrophoresis tank. The apparatus will be connected to the power pack and will be run at 70 V until the sample reached the separating gel. The voltage applied will be increased to 90V at this point. Electrophoresis will be stopped when the marker dye reached near the end of the gel. After electrophoretic separation, the gel will be stained with Coomassie blue solution (0.01% Coomassie brilliant blue R 250, 50% (v/v) methanol, and 10% (v/v) glacial acetic acid) for 3 h at room temperature and subsequently destained in the destaining solution (50% (v/v) methanol and 10% (v/v) acetic acid) for 2 h. The gel image will be captured and analyzed by a gel documentation system (Alpha Innotech), using Alpha Ease software.

Measurement of Parameters of Mitochondrial Function

Preparation of Kidney Homogenate

The kidney tissue obtained will be will behed in ice-cold saline, decapsulated, and minced into small pieces using a pair of sharp scissors, and immediately homogenized (10% w/v) in the homogenization buffer containing 0.05 M HEPES and 125 mM KCL pH 7.4, using a Potter-Elvehjem homogenizer at 5000 rpm for 3 min (10-15 strokes). The homogenates will be centrifuged at 7500 rpm for 10 min. The supernatant will be used for the biochemical assays.

Isolation of Kidney Mitochondria

The kidney tissues will be homogenized (5%) using the homogenizing buffer consisting of 220 mM Mannitol/70 mM sucrose/5 mM Tris/1 mM EGTA; pH 7.4. The homogenates will be centrifuged at 4000 Å~g for 10 min, and the nuclear pellet will be discarded. Crude mitochondrial fractions will be obtained by centrifuging at 12,000× for 20 min, and the pellet will be will washed thrice with wash buffer containing 220 mM mannitol/70 mM sucrose/20 mM HEPES; pH 7.4. The final pellet will be suspended in the same buffer. The purity of the mitochondria will be established by enrichment of marker enzyme, succinate dehydrogenase. The isolated mitochondria will be used for assessing their function and also for measuring the activities of mitochondria.

Mitochondrial Swelling

Swelling of mitochondria will be determined by following the decrease in the absorbance at 540 nm for 10 min. Mitochondrial suspension will be added to a cuvette containing buffer (250 mM sucrose/5 mM HEPES, pH 7.4). The combination will be quickly mixed, and the change in the absorbance will be measured at 540 nm for 10 min in a spectrophotometer.

Example 301: Pharmaceutical Compositions

The compositions described below are presented with a compound of Formula (I)-(Vb) for illustrative purposes.

Example 301a: Parenteral Composition

To prepare a parenteral pharmaceutical composition suitable for administration by injection, 100 mg of a compound of Formula ((I)-(Vb) is dissolved in DMSO and then mixed with 10 mL of 0.9% sterile saline. The mixture is incorporated into a dosage unit form suitable for administration by injection.

Example 301b: Oral Composition

To prepare a pharmaceutical composition for oral delivery, 100 mg of a compound of Formula (I)-(Vb) is mixed with 750 mg of starch. The mixture is incorporated into an oral dosage unit for, such as a hard gelatin capsule, which is suitable for oral administration.

Example 301c: Sublingual (Hard Lozenge) Composition

To prepare a pharmaceutical composition for buccal delivery, such as a hard lozenge, mix 100 mg of a compound of Formula (I)-(Vb) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 301d: Inhalation Composition

To prepare a pharmaceutical composition for inhalation delivery, 20 mg of a compound of Formula (I)-(Vb) is mixed with 50 mg of anhydrous citric acid and 100 mL of 0.9% sodium chloride solution. The mixture is incorporated into an inhalation delivery unit, such as a nebulizer, which is suitable for inhalation administration.

Example 301e: Rectal Gel Composition

To prepare a pharmaceutical composition for rectal delivery, 100 mg of a compound of Formula (I)-(Vb) is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example 301f: Topical Gel Composition

To prepare a pharmaceutical topical gel composition, 100 mg of a compound of (I)-(Vb) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

At least some of the chemical names of compounds of the invention as given and set forth in this application, may have been generated on an automated basis by use of a commercially available chemical naming software program, and have not been independently verified In the instance where the indicated chemical name and the depicted structure differ, the depicted structure will control. In the chemical structures where a chiral center exists in a structure but no specific stereochemistry is shown for the chiral center, both enantiomers associated with the chiral structure are encompassed by the structure.

REFERENCES

1) Breyer M D, Susztak K. The next generation of therapeutics for chronic kidney disease. Nat Rev Drug Discov. 2016 August; 15(8):568-88
2) Uchino S. The epidemiology of acute renal failure in the world. Curr Opin CritCare. 2006 December; 12(6):538-43
3) Chertow G M, Burdick E, Honour M, Bonventre J V, Bates D W. Acute kidney injury, mortality, length of stay, and costs in hospitalized patients. J Am Soc Nephrol. 2005 November; 16(11):3365-70.
4) Uchino S, Kellum J A, Bellomo R, Doig G S, Morimatsu H, Morgera S, Schetz M, Tan I, Bouman C, Macedo E, Gibney N, Tolwani A, Ronco C; Beginning and Ending Supportive Therapy for the Kidney (BEST Kidney) Investigators. Acute renal failure in critically ill patients: a multinational, multicenter study. JAMA. 2005 Aug. 17; 294(7):813-8
5) Mehta R L, Pascual M T, Soroko S, Savage B R, Himmelfarb J, Ikizler T A, Paganini E P, Chertow G M; Program to Improve Care in Acute Renal Disease. Spectrum of acute renal failure in the intensive care unit: the PICARD experience. Kidney Int. 2004 October; 66(4): 1613-21
6) Pannu N, Nadim M K. An overview of drug-induced acute kidney injury. Crit Care Med. 2008 April; 36(4 Suppl:5216-23)
7) Awdishu L, Mehta R L. The 6R's of drug induced nephrotoxicity. BMC Nephrol. 2017 Apr. 3; 18(1):124
8) Ramamoorthy H, Abraham P, Isaac B. Mitochondrial dysfunction and electron transport chain complex defect in a rat model of tenofovir disoproxil fumarate nephrotoxicity. J Biochem Mol Toxicol. 2014 June; 28(6):246-55

What is claimed is:

1. A method for treating a disease or a condition related to kidney in a mammal, wherein the method comprises administering to the mammal an effective disease-treating or condition-treating amount of a compound according to formula (Va) or formula (Vb):

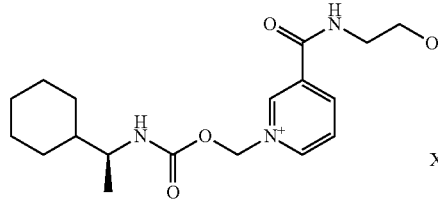

(Va)

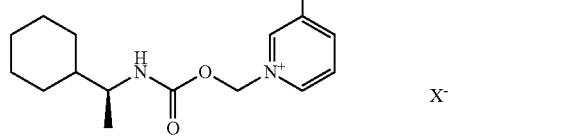

or (Vb)

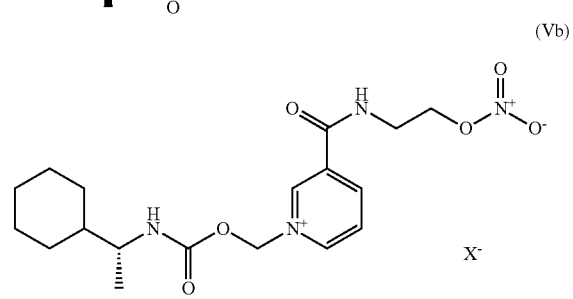

or a pharmaceutical composition thereof;
wherein X⁻ is a counter ion, and
wherein the disease or condition related to kidney is chronic kidney disease.

2. The method according to claim 1, wherein X⁻ is F⁻, Cl⁻, Br⁻, I⁻, or MeSO₂O⁻.

3. The method according to claim 1, wherein the pharmaceutical composition comprises a pharmaceutically acceptable excipient.

4. The pharmaceutical composition of claim 3 that is formulated for a route of administration selected from oral administration, parenteral administration, buccal administration, nasal administration, topical administration, or rectal administration.

5. The method of claim 1, wherein the compound of formula (Va) or formula (Vb) is administered orally.

6. The method of claim 1, wherein the compound is according to formula (Va):

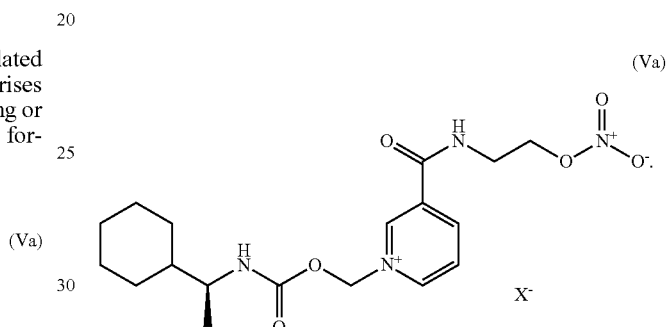

7. The method of claim 1, wherein the compound is according to formula (Vb):

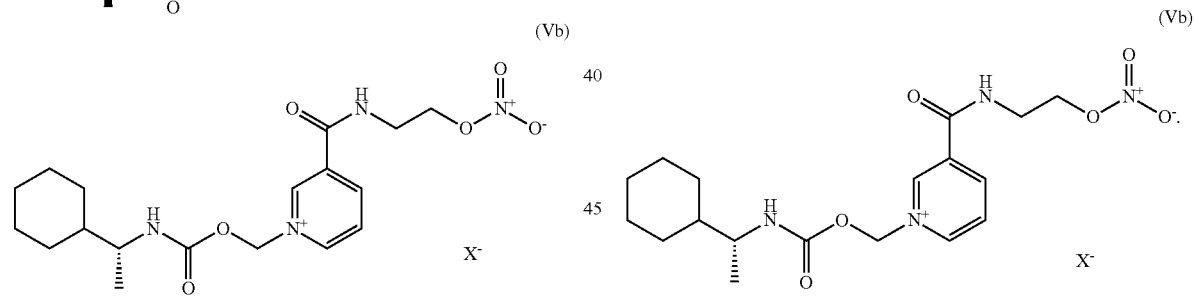

8. The method according to claim 1, wherein X⁻ is Cl⁻ or I⁻.

9. The method according to claim 1, wherein X⁻ is I⁻.

10. The method according to claim 4, wherein the parenteral administration is selected form intravenous, subcutaneous, or intramuscular.

11. The method of claim 1, wherein the pharmaceutical composition is a non-aqueous formulation comprising one or more carriers selected from the group consisting of one or more polyols and ethanol.

12. The method of claim 10, wherein the one or more polyols are selected from propylene glycol, polyethylene glycol, cremophor, and glycerol.

13. The method of claim 10, wherein the compound is chemically stable having a purity of at least 95%.

14. The method of claim 12, wherein the purity is at least 99%.

* * * * *

SEQUENCE LISTING

```
<160> NUMBER OF SEQ ID NOS: 6

<210> SEQ ID NO 1
<211> LENGTH: 23
<212> TYPE: DNA
<213> ORGANISM: artificial sequence
<220> FEATURE:
<223> OTHER INFORMATION: SUR2A forward primer

<400> SEQUENCE: 1
tgagggtatt ttagtggagt gtg                                          23

<210> SEQ ID NO 2
<211> LENGTH: 22
<212> TYPE: DNA
<213> ORGANISM: Artificial Sequence
<220> FEATURE:
<223> OTHER INFORMATION: SUR2A Reverse Primer

<400> SEQUENCE: 2
caaagtggaa aagaggccat tc                                           22

<210> SEQ ID NO 3
<211> LENGTH: 21
<212> TYPE: DNA
<213> ORGANISM: Artificial Sequence
<220> FEATURE:
<223> OTHER INFORMATION: SUR2B Forward Primer

<400> SEQUENCE: 3
tggtgacaat agctcatcga g                                            21

<210> SEQ ID NO 4
<211> LENGTH: 21
<212> TYPE: DNA
<213> ORGANISM: Artificial Sequence
<220> FEATURE:
<223> OTHER INFORMATION: SUR2B Reverse Primer

<400> SEQUENCE: 4
tccattttcc tgagccaaga g                                            21

<210> SEQ ID NO 5
<211> LENGTH: 22
<212> TYPE: DNA
```

```
<213> ORGANISM: Artificial Sequence
<220> FEATURE:
<223> OTHER INFORMATION: actin forward primer

<400> SEQUENCE: 5
tgagatgcgt tgttacagga ag                                            22

<210> SEQ ID NO 6
<211> LENGTH: 20
<212> TYPE: DNA
<213> ORGANISM: Artificial Sequence
<220> FEATURE:
<223> OTHER INFORMATION: actin reverse primer

<400> SEQUENCE: 6
gtggacttgg gagaggactg                                               20
```